US008535241B2

(12) United States Patent
Bullington et al.

(10) Patent No.: US 8,535,241 B2
(45) Date of Patent: Sep. 17, 2013

(54) FLUID DIVERSION MECHANISM FOR BODILY-FLUID SAMPLING

(71) Applicants: Gregory Bullington, San Francisco, CA (US); Richard G. Patton, Seattle, WA (US); Shan Gaw, Seattle, WA (US); Jay Miazga, Seattle, WA (US)

(72) Inventors: Gregory Bullington, San Francisco, CA (US); Richard G. Patton, Seattle, WA (US); Shan Gaw, Seattle, WA (US); Jay Miazga, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

(21) Appl. No.: 13/650,554

(22) Filed: Oct. 12, 2012

(65) Prior Publication Data
US 2013/0116599 A1   May 9, 2013

Related U.S. Application Data

(60) Provisional application No. 61/546,954, filed on Oct. 13, 2011.

(51) Int. Cl.
*A61B 5/00* (2006.01)
*B65D 81/00* (2006.01)
*A61M 1/00* (2006.01)
*A61M 5/00* (2006.01)
*A61M 5/14* (2006.01)

(52) U.S. Cl.
USPC ............. 600/579; 600/573; 604/30; 604/33; 604/246; 604/249; 604/256

(58) Field of Classification Search
USPC ............. 600/573, 576, 577–581; 604/27, 604/30, 33, 34, 246, 248, 249, 256
See application file for complete search history.

(56) References Cited

U.S. PATENT DOCUMENTS

| 2,707,953 | A | 5/1955  | Ryan           |
|-----------|---|---------|----------------|
| 3,013,557 | A | 12/1961 | Pallotta       |
| 3,098,016 | A | 7/1963  | Cooper et al.  |
| 3,382,865 | A | 5/1968  | Worral, Jr.    |
| 3,405,706 | A | 10/1968 | Cinqualbre     |
| 3,494,351 | A | 2/1970  | Horn           |
| 3,577,980 | A | 5/1971  | Cohen          |
| 3,648,684 | A | 3/1972  | Barnwell et al.|
| 3,848,579 | A | 11/1974 | Villa-Real     |
| 3,937,211 | A | 2/1976  | Merten         |

(Continued)

OTHER PUBLICATIONS

International Search Report and Written Opinion mailed May 16, 2008, which issued during the prosecution of International Patent Application No. PCT/US2007/087951 (8 pages).

(Continued)

*Primary Examiner* — Rene Towa
*Assistant Examiner* — Adam Eiseman
(74) *Attorney, Agent, or Firm* — Cooley LLP

(57) ABSTRACT

An apparatus includes a housing, a flow control mechanism, and an actuator. At least a portion of the flow control mechanism is movably disposed within the housing. The apparatus further includes an inlet port and an outlet port, and defines a fluid reservoir. The outlet port is fluidically coupled to a second fluid reservoir and is fluidically isolated from the first fluid reservoir. The actuator is configured to move the flow control mechanism between a first configuration, in which the inlet port is placed in fluid communication with the fluid reservoir such that the fluid reservoir receives a first flow of bodily-fluid, and a second configuration, in which the inlet port is placed in fluid communication with the outlet port.

13 Claims, 17 Drawing Sheets

(56) References Cited

U.S. PATENT DOCUMENTS

| | | | |
|---|---|---|---|
| 4,057,050 A | 11/1977 | Sarstedt | |
| 4,133,863 A | 1/1979 | Koenig | |
| 4,166,450 A | 9/1979 | Abramson | |
| 4,340,067 A | 7/1982 | Rattenborg | |
| 4,370,987 A | 2/1983 | Bazell et al. | |
| 4,444,203 A | 4/1984 | Engelman | |
| 4,459,997 A | 7/1984 | Sarstedt | |
| 4,509,534 A | 4/1985 | Tassin, Jr. | |
| 4,657,160 A * | 4/1987 | Woods et al. | 222/94 |
| 4,676,256 A | 6/1987 | Golden | |
| 4,865,583 A | 9/1989 | Tu | |
| 4,890,627 A | 1/1990 | Haber et al. | |
| 4,988,339 A | 1/1991 | Vadher | |
| 5,009,847 A | 4/1991 | Solomons | |
| 5,097,842 A | 3/1992 | Bonn | |
| 5,108,927 A | 4/1992 | Dom | |
| 5,122,129 A | 6/1992 | Olson et al. | |
| 5,269,317 A | 12/1993 | Bennett | |
| 5,330,464 A | 7/1994 | Mathias et al. | |
| 5,360,011 A | 11/1994 | McCallister | |
| 5,429,610 A | 7/1995 | Vaillancourt | |
| 5,450,856 A | 9/1995 | Norris | |
| 5,507,299 A | 4/1996 | Roland | |
| 5,577,513 A | 11/1996 | Van Vlasselaer | |
| 5,762,633 A | 6/1998 | Whisson | |
| 5,865,812 A * | 2/1999 | Correia | 604/248 |
| 5,882,318 A | 3/1999 | Boyde | |
| 5,922,551 A | 7/1999 | Durbin et al. | |
| 6,016,712 A | 1/2000 | Warden et al. | |
| 6,057,105 A | 5/2000 | Hoon et al. | |
| 6,159,164 A | 12/2000 | Neese et al. | |
| 6,210,909 B1 | 4/2001 | Guirguis | |
| 6,364,890 B1 | 4/2002 | Lum et al. | |
| 6,387,086 B2 | 5/2002 | Mathias et al. | |
| 6,403,381 B1 | 6/2002 | Mann et al. | |
| 6,626,884 B1 * | 9/2003 | Dillon et al. | 604/409 |
| 6,692,479 B2 | 2/2004 | Kraus et al. | |
| 6,746,420 B1 | 6/2004 | Prestidge et al. | |
| 6,913,580 B2 | 7/2005 | Stone | |
| 7,044,941 B2 | 5/2006 | Mathias et al. | |
| 7,087,047 B2 | 8/2006 | Kraus et al. | |
| 7,335,188 B2 * | 2/2008 | Graf | 604/317 |
| 7,744,573 B2 * | 6/2010 | Gordon et al. | 604/248 |
| 8,197,420 B2 | 6/2012 | Patton | |
| 8,231,546 B2 | 7/2012 | Patton | |
| 8,337,418 B2 * | 12/2012 | Patton | 600/573 |
| 2002/0002349 A1 | 1/2002 | Flaherty et al. | |
| 2002/0183651 A1 | 12/2002 | Hyun | |
| 2003/0055381 A1 | 3/2003 | Wilkinson | |
| 2003/0208151 A1 * | 11/2003 | Kraus et al. | 604/4.01 |
| 2004/0010228 A1 | 1/2004 | Swenson et al. | |
| 2004/0054333 A1 | 3/2004 | Theeuwes et al. | |
| 2004/0147855 A1 | 7/2004 | Marsden | |
| 2005/0004524 A1 | 1/2005 | Newby et al. | |
| 2005/0240161 A1 | 10/2005 | Crawford | |
| 2005/0245885 A1 | 11/2005 | Brown | |
| 2005/0281713 A1 | 12/2005 | Hampsch et al. | |
| 2006/0287639 A1 | 12/2006 | Sharp | |
| 2008/0108954 A1 * | 5/2008 | Mathias et al. | 604/248 |
| 2008/0145933 A1 * | 6/2008 | Patton | 435/379 |

OTHER PUBLICATIONS

Patton et al., "Innovation for Reducing Blood Culture Contamination: Initial Specimen Diversion Technique," Journal of Clinical Microbiology, Dec. 2010, p. 4501-4503.

Wagner et al. "Diversion of Initial Blood Flow to Prevent Whole-Blood Contamination by Skin Surface Bacteria: an in vitro model," Transfusion, vol. 40, Mar. 2000, pp. 335-3381.

Office Action for U.S. Appl. No. 11/955,635, mailed Jul. 22, 2010, 11 pages.

Office Action for U.S. Appl. No. 11/955,635, mailed Dec. 3, 2010, 11 pages.

Office Action for U.S. Appl. No. 13/335,241, mailed Apr. 20, 2012, 12 pages.

Office Action for U.S. Appl. No. 13/458,508, mailed Jul. 24, 2012, 13 pages.

\* cited by examiner

FLUID DIVERSION MECHANISM FOR BODILY-FLUID SAMPLING

CROSS REFERENCE TO RELATED APPLICATIONS

This application claims the benefit of and priority to U.S. Provisional Application Ser. No. 61/546,954, filed Oct. 13, 2011, entitled, "Innovation for Reducing Blood Culture Contamination: Initial Specimen Diversion Technique," the disclosure of which is hereby incorporated by reference in its entirety.

BACKGROUND

Embodiments described herein relate generally to the parenteral procurement of bodily-fluid samples, and more particularly to devices and methods for parenterally-procuring bodily-fluid samples with reduced contamination from microbes or other contaminants exterior to the bodily-fluid source, such as dermally-residing microbes.

Health care practitioners routinely perform various types of microbial tests on patients using parenterally-obtained bodily-fluids. Patient samples (e.g., bodily-fluids) are sometimes tested for the presence of one or more potentially undesirable microbes, such as bacteria, fungi, or yeast (e.g., *Candida*). Microbial testing may include incubating patient samples in one or more sterile vessels containing culture media that is conducive to microbial growth. Generally, when microbes tested for are present in the patient sample, the microbes flourish over time in the culture medium. After a pre-determined amount of time (e.g., a few hours to several days), the culture medium can be tested for the presence of the microbes. The presence of microbes in the culture medium suggests the presence of the same microbes in the patient sample which, in turn, suggests the presence of the same microbes in the bodily-fluid of the patient from which the sample was obtained. Accordingly, when microbes are determined to be present in the culture medium, the patient may be prescribed one or more antibiotics or other treatments specifically designed to treat or otherwise remove the undesired microbes from the patient.

Patient samples, however, can sometimes become contaminated during procurement. One way in which contamination of a patient sample may occur is by the transfer of microbes from a bodily surface (e.g., dermally-residing microbes) dislodged during needle insertion into a patient and subsequently transferred to a culture medium with the patient sample. The bodily surface microbes may be dislodged either directly or via dislodged tissue fragments, hair follicles, sweat glands and other adnexal structures. The transferred microbes may thrive in the culture medium and eventually yield a positive microbial test result, thereby falsely indicating the presence of such microbes in vivo. Such inaccurate results are a concern when attempting to diagnose or treat a suspected illness or condition. For example, false positive results from microbial tests may result in the patient being unnecessarily subjected to one or more anti-microbial therapies, which may cause serious side effects to the patient including, for example, death, as well as produce an unnecessary burden and expense to the health care system.

As such, a need exists for improved bodily-fluid transfer devices and methods that reduce microbial contamination in bodily-fluid test samples.

SUMMARY

Devices for parenterally-procuring bodily-fluid samples with reduced contamination from microbes exterior to the bodily-fluid source, such as dermally-residing microbes, are described herein. In some embodiments, an apparatus includes a housing, a flow control mechanism, and an actuator. At least a portion of the flow control mechanism is movably disposed within the housing. The apparatus further includes an inlet port and an outlet port, and defines a fluid reservoir. The outlet port is fluidically coupled to a second fluid reservoir and is fluidically isolated from the first fluid reservoir. The actuator is configured to move the flow control mechanism between a first configuration, in which the inlet port is placed in fluid communication with the fluid reservoir such that the fluid reservoir receives a first flow of bodily-fluid, and a second configuration, in which the inlet port is placed in fluid communication with the outlet port.

DETAILED DESCRIPTION

Figure 1:
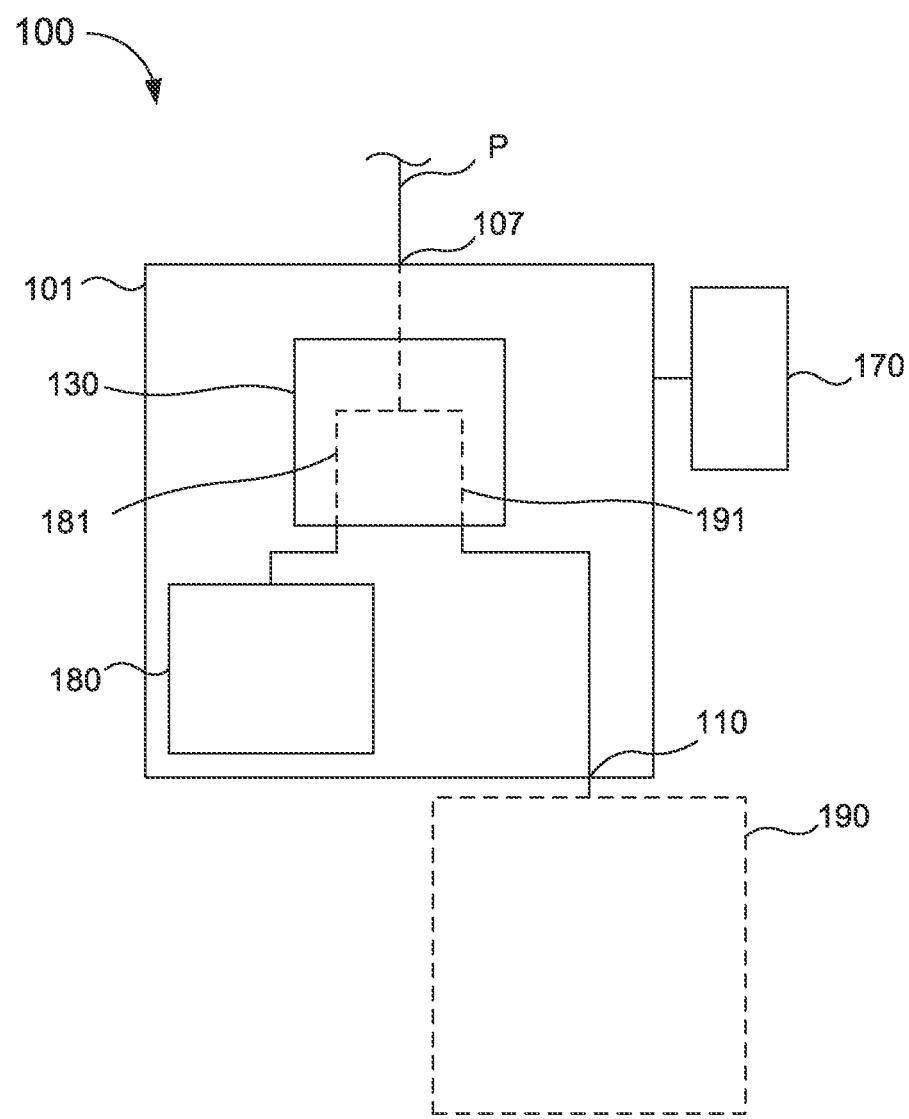
FIG. 1 is a schematic illustration of a bodily-fluid transfer device according to an embodiment.
Figure 2:
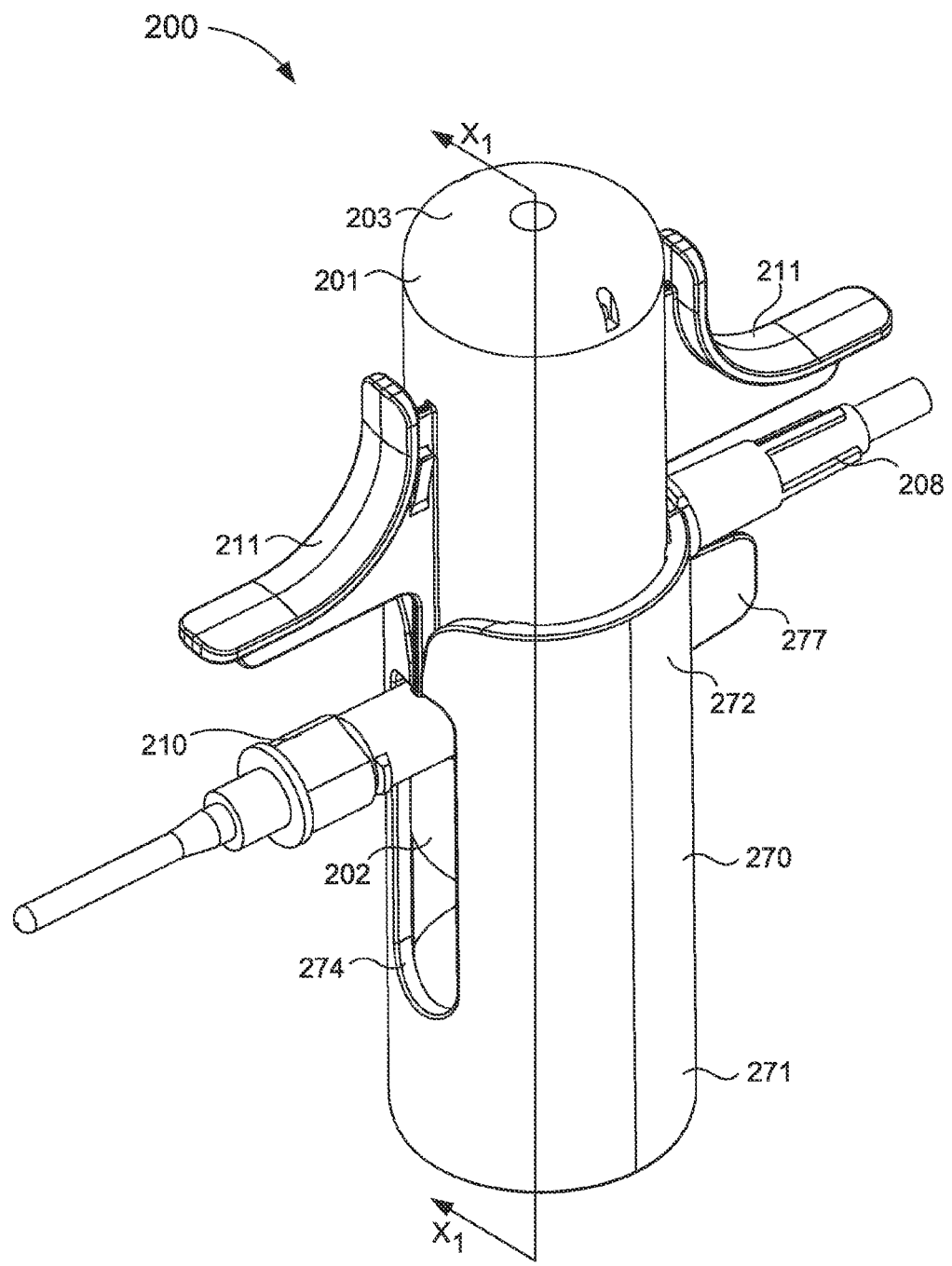
FIG. 2 is a perspective view of a bodily-fluid transfer device according to an embodiment.
Figure 3:
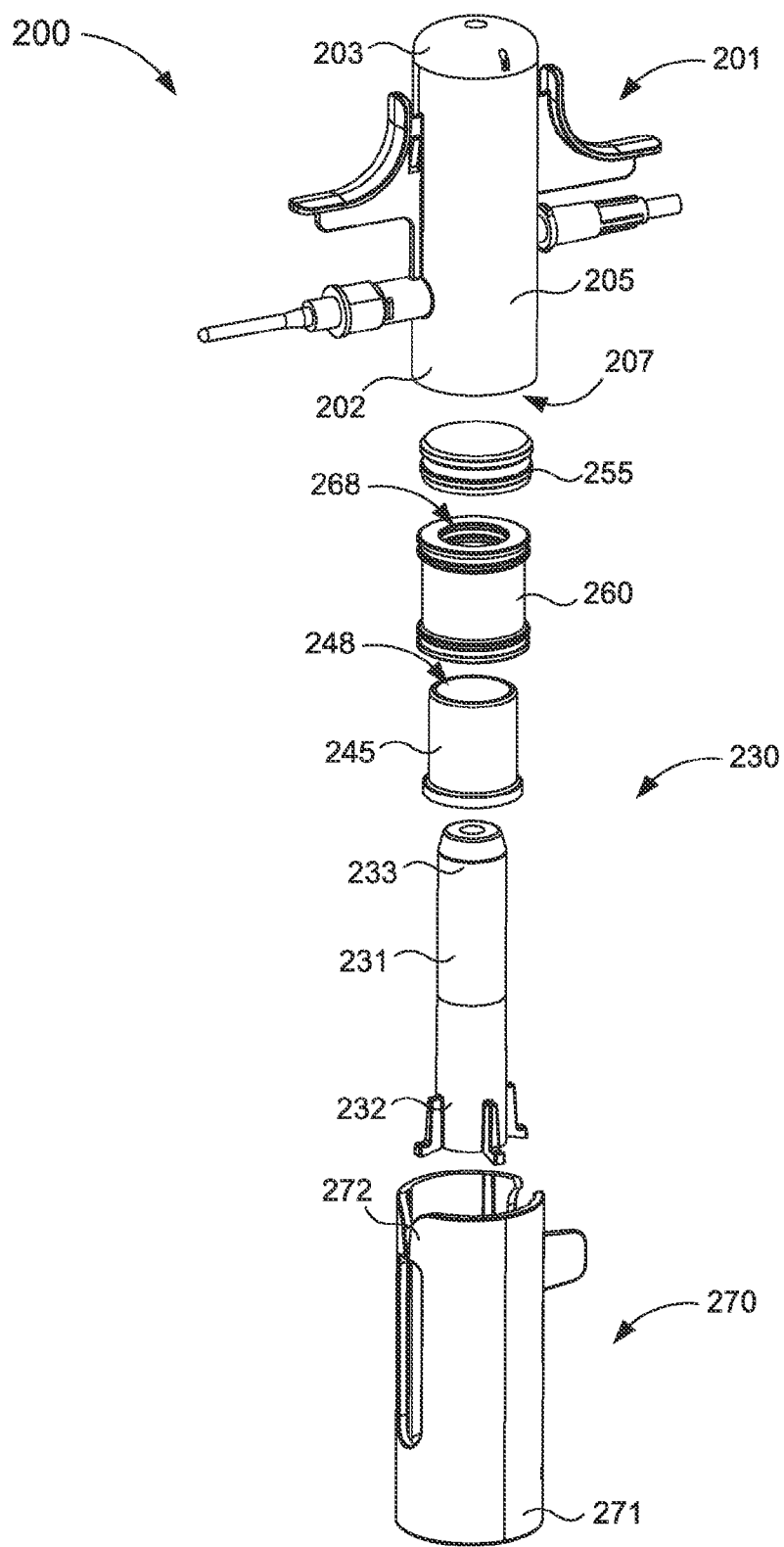
FIG. 3 is an exploded view of the bodily-fluid transfer device of FIG. 2.

Devices for parenterally-procuring bodily-fluid samples with reduced contamination from microbes exterior to the bodily-fluid source, such as dermally-residing microbes, are described herein. In some embodiments, an apparatus includes a housing, a flow control mechanism, and an actuator. At least a portion of the flow control mechanism is movably disposed within the housing. The apparatus further includes an inlet port and an outlet port, and defines a first fluid reservoir. The outlet port is fluidically coupleable to a second fluid reservoir, fluidically isolated from the first fluid reservoir. The actuator is configured to move the flow control mechanism between a first configuration, in which the inlet port is placed in fluid communication with the first fluid reservoir such that the first fluid reservoir receives a flow of bodily-fluid, and a second configuration, in which the inlet port is placed in fluid communication with the outlet port such that the second fluid reservoir can receive a flow of bodily-fluid.

In some embodiments, a bodily-fluid transfer device can be configured to selectively divert a first, predetermined amount of a flow of a bodily-fluid to a first fluid reservoir before permitting the flow of a second amount of the bodily-fluid into a second fluid reservoir. In this manner, the second amount of bodily-fluid can be used for diagnostic or other testing, while the first amount of bodily-fluid, which may contain microbes from a bodily surface, is isolated from the bodily-fluid to be tested.

In some embodiments, a bodily-fluid transfer device is configured to automatically move from a first configuration to a second configuration, for example, without requiring an input or other action by a health care practitioner. In some embodiments, the bodily-fluid transfer device prevents bodily-fluid from flowing or otherwise being introduced into a second fluid reservoir before at least a first amount of bodily-fluid (e.g., a predetermined amount) is first introduced into a first fluid reservoir.

As referred to herein, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used in this specification, the words "proximal" and "distal" refer to the direction closer to and away from, respectively, a user who would place the device into contact with a patient. Thus, for example, the end of a device being actuated by the user would be the proximal end, while the opposite end of the device would be the distal end of the device.

As used in this specification, the terms "first, predetermined amount" and "first amount" describe a given amount of bodily-fluid configured to be received or contained by a pre-sample reservoir (also referred to herein as a "first reservoir"). While the term "first amount" does not explicitly describe a predetermined amount, it should be understood that the first amount is the first, predetermined amount unless explicitly described differently.

FIG. 1 is a schematic illustration of a portion of a bodily-fluid transfer device 100, according to an embodiment. Generally, the bodily-fluid transfer device 100 (also referred to herein as "fluid transfer device" or "transfer device") is configured to permit the withdrawal of bodily-fluid from a patient such that a first portion or amount of the withdrawn fluid is diverted away from a second portion or amount of the withdrawn fluid that is to be used as a biological sample, such as for testing for the purpose of medical diagnosis and/or treatment. In other words, the transfer device 100 is configured to transfer a first, predetermined amount of a bodily-fluid to a first collection reservoir and a second amount of bodily-fluid to one or more bodily-fluid collection reservoirs fluidically isolated from the first collection reservoir, as described in more detail herein.

The transfer device 100 includes a housing 101, an inlet port 107, an outlet port 110, a flow control mechanism 130, an actuator 170, a first fluid reservoir 180 (also referred to herein as "first reservoir"), and optionally a second fluid reservoir 190 (also referred to herein as "second reservoir"), different than the first reservoir 180. The housing 101 can house at least a portion of the flow control mechanism 130 and the first reservoir 180. In some embodiments, the housing 101 can also house at least a portion of the actuator 170 and/or at least a portion of the second reservoir 190. The housing 101 can be any suitable shape, size, or configuration and is described in further detail herein with respect to specific embodiments.

In some embodiments, the inlet port 107 and the outlet port 110 can be included in (e.g., monolithically formed with) or coupled to the housing 101. In other embodiments, the inlet port 107 and the outlet port 110 can be included in or coupled to the flow control mechanism 130 and can extend through a portion of the housing 101. As shown in FIG. 1, the inlet port 107 can be, at least temporarily, physically and fluidically coupled to a medical device defining a pathway P for withdrawing and/or conveying the bodily-fluid from the patient to the transfer device 100. For example, the inlet port 107 can be a Luer-Lok® or the like configured to be physically and fluidically coupled to a needle, a cannula, or other lumen-containing device. In other embodiments, the inlet port 107 can be monolithically formed with at least a portion of the lumen-containing device. In this manner, the inlet port 107 can receive the bodily-fluid from the patient via the pathway P. The outlet port 110 is configured to be fluidically coupled to the second fluid reservoir 190, as further described herein.

The first reservoir 180 can be any suitable reservoir for containing a bodily-fluid. For example, in some embodiments, the first reservoir 180 can be formed by a portion of the flow control mechanism 130 (e.g., defined by a set of walls of the flow control mechanism 130). In some embodiments, the first reservoir 180 can be formed or defined by a portion of the flow control mechanism 130 and a portion of the housing 101. In other embodiments, the first reservoir 180 can be self-contained (e.g., such as a bladder or the like) and be disposed within a portion of the housing 101 and/or the flow control mechanism 130. In some embodiments, the first reservoir 180 can be a pre-sample reservoir such as those described in detail in U.S. Pat. No. 8,197,420 ("the '420 patent"), the disclosure of which is incorporated herein by reference in its entirety. In this manner, the first reservoir 180 can be, at least temporarily, placed in fluid communication with the inlet port 107 such that the first reservoir 180 can receive and contain the first, predetermined amount of the bodily-fluid. In some embodiments, the first reservoir 180 is configured to contain the first amount of the bodily-fluid such that the first amount is fluidically isolated from a second amount of the bodily-fluid (different than the first amount of bodily-fluid) that is subsequently withdrawn from the patient.

The second reservoir 190 can be any suitable reservoir for containing a bodily-fluid, including, for example, a sample reservoir as described in the '420 patent incorporated by reference above. In some embodiments, the second reservoir 190 can be substantially similar to or the same as known sample containers such as, for example, a Vacutainer® or the like. The second reservoir 190 is configured to be fluidically coupled to the outlet port 110 of the transfer device 100. For example, in some embodiments, the second reservoir 190 is physically (either directly or via an intervening structure such as sterile flexible tubing) and fluidically coupled to the outlet port 110. In other embodiments, the second reservoir 190 can be moved relative to the outlet port 110 to place the second reservoir 190 in fluid communication with the outlet port 110, as described herein with respect to specific embodiments.

The second reservoir 190 is configured to receive and contain the second amount of the bodily-fluid. For example, the second amount of bodily-fluid can be an amount withdrawn from the patient subsequent to withdrawal of the first amount. In some embodiments, the second reservoir 190 is configured to contain the second amount of the bodily-fluid such that the second amount is fluidically isolated from the first amount of the bodily-fluid. As used in this specification, the term "second amount" describes an amount of bodily-fluid configured to be received or contained by the second reservoir 190. In some embodiments, the second amount can be any suitable amount of bodily-fluid and need not be predetermined. In other embodiments, the second amount received and contained by the second reservoir 190 is a second predetermined amount.

The flow control mechanism 130 of the transfer device 100 is movably disposed within the housing 101 between a first configuration and a second configuration and defines, at least partially, a first fluid flow path 181 and a second fluid flow path 191, as described in further detail herein. The flow control mechanism 130 can be any suitable shape, size, or configuration. For example, in some embodiments, the flow control mechanism 130 can include multiple components. In such embodiments, a first set of one or more components can move together with and/or relative to a second set of one or more components such that the flow control mechanism 130 is moved between the first configuration and the second configuration.

The actuator 170 of the transfer device 100 can be operably coupled to the flow control mechanism 130 (e.g., either directly or indirectly via an intervening structure). In this manner, the actuator 170 can be configured to move the flow control mechanism 130 relative to the housing 101 between the first configuration and the second configuration. For example, the actuator 170 can be movable between a first position corresponding to the first configuration of the flow control mechanism 130, and a second position, different than the first position, corresponding to the second configuration of the flow control mechanism 130. In some embodiments, the actuator 170 is configured for uni-directional movement. For example, the actuator 170 can be moved from its first position to its second position, but cannot be moved from its second position to its first position. In this manner, the flow control mechanism 130 is prevented from being moved to its second configuration before its first configuration, thus requiring that the first amount of the bodily-fluid be directed to the first reservoir 180 and not the second reservoir 190, as further described herein.

In some embodiments, the actuator 170 can move the flow control mechanism 130 in a translational motion between the first configuration and the second configuration. For example, in some embodiments, the flow control mechanism 130 can be in the first configuration when the flow control mechanism 130 (or components included therein) is in a proximal position relative to the housing 101. In such embodiments, the actuator 170 can be actuated to move the flow control device 130 in the distal direction to a distal position relative to the housing 101, thereby placing the flow control mechanism 130 in the second configuration. In other embodiments, the actuator 170 can be actuated to move the flow control mechanism 130 in any suitable motion between the first configuration and the second configuration (e.g., rotational). Examples of suitable actuators are described in more detail herein with reference to specific embodiments.

As described above, when the actuator 170 is in the first position and the flow control mechanism 130 is in the first configuration, the inlet port 107 is placed in fluid communication with the first fluid reservoir 180 and the outlet port 110 is fluidically isolated from the inlet port 107. More specifically, the bodily-fluid can flow within the first fluid flow path 181 between the inlet port 107 and the first reservoir 180 such that the first reservoir 180 receives the first amount of the bodily-fluid. Similarly, when the actuator 170 is moved to the second position to place the flow control mechanism 130 in the second configuration, the first reservoir 180 is fluidically isolated from the inlet port 107 and the outlet port 110 is placed in fluid communication with the inlet port 107. More specifically, the bodily-fluid can flow within the second fluid flow path 191 between the inlet port 107 and the outlet port 110 such that the second reservoir 190 receives the second amount of the bodily-fluid.

In some embodiments, the transfer device 100 is configured such that the first amount of bodily-fluid need be conveyed to the first reservoir 180 before the transfer device 100 will permit the flow of the second amount of bodily-fluid to be conveyed through the outlet port 110 to the second reservoir 190. In this manner, the transfer device 100 can be characterized as requiring compliance by a health care practitioner regarding the collection of the first, predetermined amount (e.g., a pre-sample) prior to a collection of the second amount (e.g., a sample) of bodily-fluid. Similarly stated, the transfer device 100 can be configured to prevent a health care practitioner from collecting the second amount, or the sample, of bodily-fluid into the second reservoir 190 without first diverting the first amount, or pre-sample, of bodily-fluid to the first reservoir 180. In this manner, the health care practitioner is prevented from including (whether intentionally or unintentionally) the first amount of bodily-fluid, which is more likely to contain bodily surface microbes, in the bodily-fluid sample to be used for analysis.

In some embodiments, the actuator 170 can have a third position and/or a fourth position, different than the first and second positions, which corresponds to a third configuration of the flow control mechanism 130. When in the third configuration, the flow control mechanism 130 can fluidically isolate the inlet port 107 from both the first reservoir 180 and the outlet port 110 simultaneously. Therefore, when the flow control mechanism 130 is in its third configuration, flow of bodily-fluid from the inlet port 107 to either the first reservoir 180 or the second reservoir 190 is prevented. For example, the actuator 170 can be actuated to place the flow control mechanism 130 in the first configuration such that a bodily-fluid can flow from the inlet port 107 to the first reservoir 180, then moved to the second configuration such that the bodily-fluid can flow from the inlet port 107 to the second reservoir 190, then moved to the third configuration to stop the flow of bodily-fluid into and/or through the outlet port 110. In some embodiments, the flow control mechanism 130 can be moved to the third configuration between the first configuration and the second configuration. In some embodiments, the flow control mechanism 130 can be in the third configuration before being moved to either of the first configuration or the second configuration.

The transfer device 100 is one example of a device that can be used to implement the Initial Specimen Diversion Technique ("ISDT") described in U.S. Provisional Application Ser. No. 61/546,954 incorporated by reference above. For example, in some embodiments, the transfer device 100 can be used by a phlebotomist (or technician otherwise trained in withdrawing a bodily fluid from a patient) for the collection of a sample blood culture. In some embodiments, phlebotomist or technician can use an alternative transfer device or other medical equipment to implement the ISDT as described herein. For example, the phlebotomist can prepare a venipuncture site with a skin antisepsis (e.g., 2% chlorhexidine, 70% alcohol) and insert a needle into the vein of the patient such that a flow of blood is transferred away from the patient. The phlebotomist can divert a first, predetermined amount of blood to a first reservoir, as described herein. The first amount of blood can, for example, be sufficiently large such that dermally-residing microbes which may have been dislodged into the needle during the insertion of the needle into the vein may be washed into the first reservoir, thereby reducing the microbial contamination in the blood that is subsequently used as one or more samples for cultured microbial tests.

In some embodiments, the first amount of blood disposed within the first reservoir (e.g., a pre-sample reservoir) can be associated with a size of a second reservoir and/or can be based on the desired volume of sample blood. For example, in some embodiments, the first amount can be approximately 0.5 mL to approximately 5 mL. In other embodiments, the first amount can be approximately 0.5 mL to approximately 2.0 mL of the bodily fluid. In still other embodiments, such as those used on pediatric patients, the first amount can be approximately 0.1 mL to approximately 0.5 mL of the bodily fluid. Thus, the first amount can be sufficiently large to adequately collect undesirable microbes while maintaining a substantially low risk of inducing nosocomial anemia in, for example, fragile patients.

With the first amount of blood disposed within the first reservoir, the phlebotomist can fluidically isolate the first reservoir and place the second reservoir in fluid communication with the needle. In this manner, the phlebotomist can transfer a second amount of blood to the second reservoir that can be substantially free from, for example, dermally-residing microbes. Thus, the second amount of blood can be used in any suitable test, such as a blood culture test, with a reduced likelihood of false positives caused by undesirable microbes.

In some embodiments, with the second amount of blood collected the phlebotomist can remove the needle from the patient and discard the first amount of blood disposed within the first reservoir. In other embodiments, the blood collected in the first reservoir can be used for conducting one or more non-culture tests, such as one or more biochemical tests, blood counts, immunodiagnostic tests, cancer-cell detection tests, or the like.

In some embodiments, the ISDT can be used to reduce contamination without impacting the specimen volume for blood culture. For example, the "diversion volume" or "pre-sample" can be collected without reducing the volume collected for blood culture sampling. Thus, the ISDT reduces contamination without impacting blood culture sensitivity (e.g., false-negatives) by, for example, minimizing the diversion volume. As described above, the ISDT can also be used to reduce contamination without inducing nosocomial anemia in fragile patients. Said another way, the ISDT and/or transfer devices can be customized for different applications to balance the many competing factors (e.g., contamination, false-negatives, nosocomial anemia, etc.) associated with bodily fluid sampling. Thus, sample contamination can be sufficiently reduced with out introducing other adverse consequences.

In some embodiments, higher diversion volumes can be used to further reduce the risk of sample contamination. For example, depending on the sensitivity of the test for which the sample is being collected, larger volumes of bodily-fluid can be diverted to further reduce the likelihood of contamination where the test is highly sensitive to dermally-residing microbes and/or other contaminants.

In some embodiments, the diversion volume can be optimized for the needle size being use to obtain the bodily-fluid sample. For example, smaller gauge needles tend to dislodge fewer dermally residing microbes, therefore, smaller diversion volumes can yield a similar contamination reduction (e.g., number of false positives). Thus, smaller needles can be used for smaller, difficult, or compromised veins/patients to reduce the diversion volume required for the IDST.

Referring now to FIGS. 2-12, a transfer device 200 includes a housing 201, a flow control mechanism 230, an actuator 270, and a fluid reservoir 280 (also referred to herein as "first fluid reservoir" or "first reservoir"). As further described herein, the transfer device 200 can be moved between a first, a second, and a third configuration to deliver a flow of a bodily-fluid that is substantially free from microbes exterior to the body, such as, for example, dermally residing microbes. The transfer device 200 can be any suitable shape, size, or configuration. For example, while shown in FIG. 2 as being substantially cylindrical, the transfer device 200 can be polygonal (rectangular, hexagonal, etc.), oval (elliptical, egg-shaped, etc.), and/or any other non-cylindrical shape.

The housing 201 includes a proximal end portion 202 and a distal end portion 203. The distal end portion 203 is a substantially closed portion of the housing 201 and includes one or more vents 214, as further described in detail herein. Moreover, a set of annular walls 205 are configured to extend from the distal end portion 203 towards the proximal end portion 202 to define an inner volume 207 therebetween. The proximal end portion 202 of the housing 201 is substantially open such that the inner volume 207 can receive at least a portion of the flow control mechanism 230 (see e.g., FIG. 3).

Figure 4:
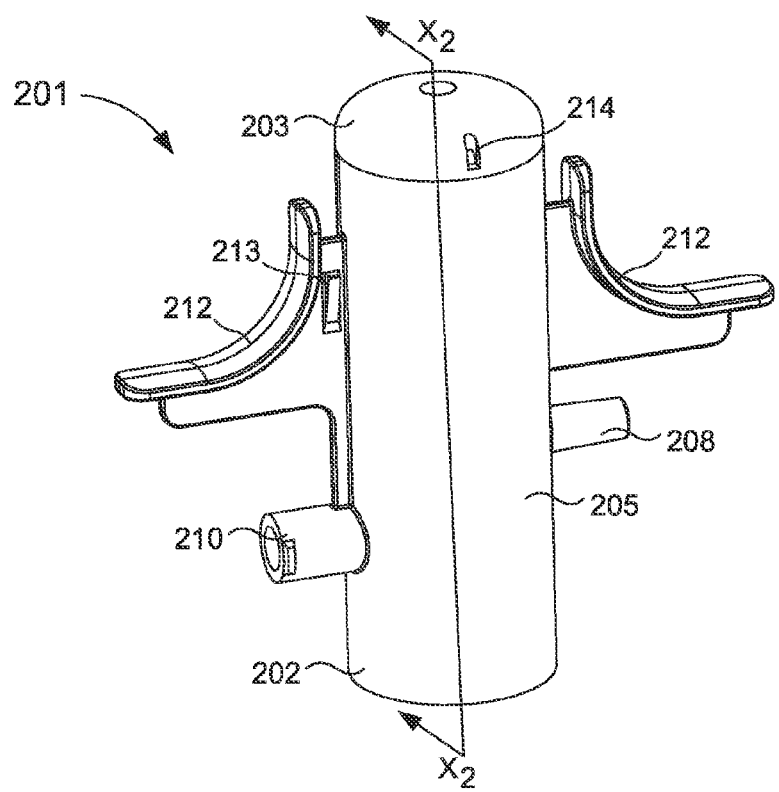
FIG. 4 is a perspective view of a housing included in the bodily-fluid transfer device illustrated in FIG. 2.
Figure 5:
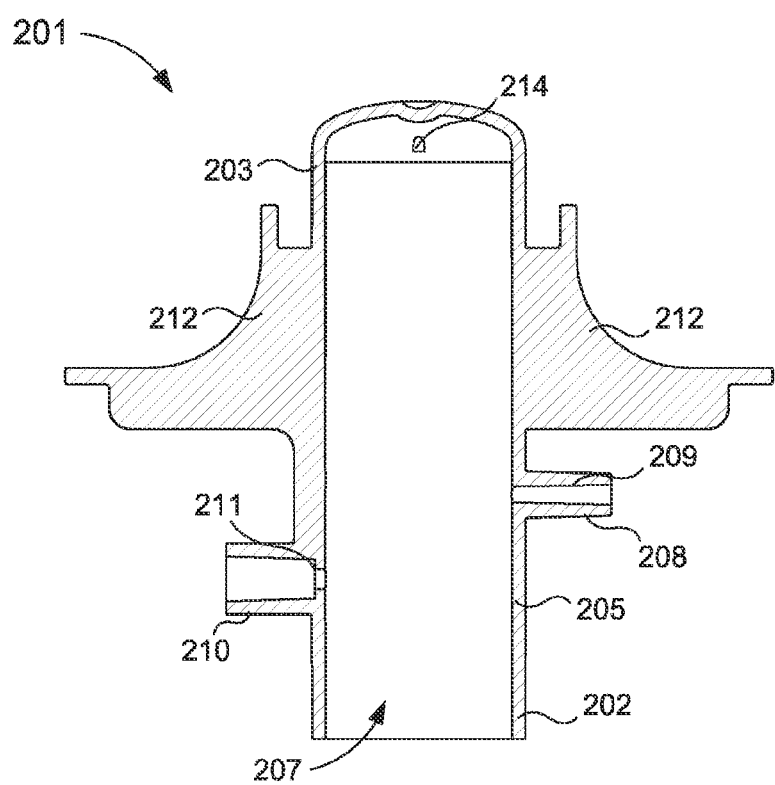
FIG. 5 is a cross-sectional view of the housing illustrated in FIG. 4 taken along the line $X_2$-$X_2$.

As shown in FIGS. 4 and 5, the housing 201 further includes an inlet port 208, an outlet port 210, and an engagement portion 212. The engagement portion 212 extends from opposite sides of an outer surface of the walls 205, as shown in FIG. 4. The engagement portion 212 includes one or more retention tabs 213 that can be placed in contact with a portion of the actuator 270 to selectively limit a movement of the actuator 270 relative to the housing 201, as further described in detail herein. In addition, the engagement portion 212 can be engaged by a user during operation to facilitate the movement of the transfer device 200 between the first, second, and third configurations, as further described herein.

The inlet port 208 included in the housing 201 is in fluid communication with the inner volume 207. More specifically, the inlet port 208 defines an inlet lumen 209 that is in fluid communication with the inner volume 207. In this manner, the inlet port 208 extends from a portion of the wall 205 defining the inner volume 207 such that the inner volume 207 can be placed in fluid communication with a volume substantially outside the housing 201, via the inlet lumen 209. The inlet port 208 can be fluidically coupled to a medical device (not shown) that defines a fluid flow pathway for withdrawing and/or conveying the bodily-fluid from a patient to the transfer device 200. For example, the inlet port 208 can be fluidically coupled to a needle or other lumen-containing device (e.g., flexible sterile tubing). Similarly stated, the inlet lumen 209 defined by the inlet port 208 is placed in fluid communication with a lumen defined by a lumen-containing device, when the lumen-containing device is coupled to the inlet port 208. Expanding further, when the lumen-containing device is disposed within a portion of a body of the patient (e.g., within a vein of the patient), the inner volume 207 of the housing 201 is placed in fluid communication with the portion of the body of the patient.

The outlet port 210 included in the housing 201 defines an outlet lumen 211. As shown in FIG. 5, the outlet lumen 211 is configured to be in fluid communication with the inner volume 207 of the housing 201 (e.g., the outlet lumen 211 extends through the wall 205 defining the inner volume 207). While not shown in FIGS. 2-12, the outlet port 210 can be fluidically coupled to an external fluid reservoir (also referred to herein as "second fluid reservoir" or "second reservoir"), as further described in detail herein.

Figure 6:
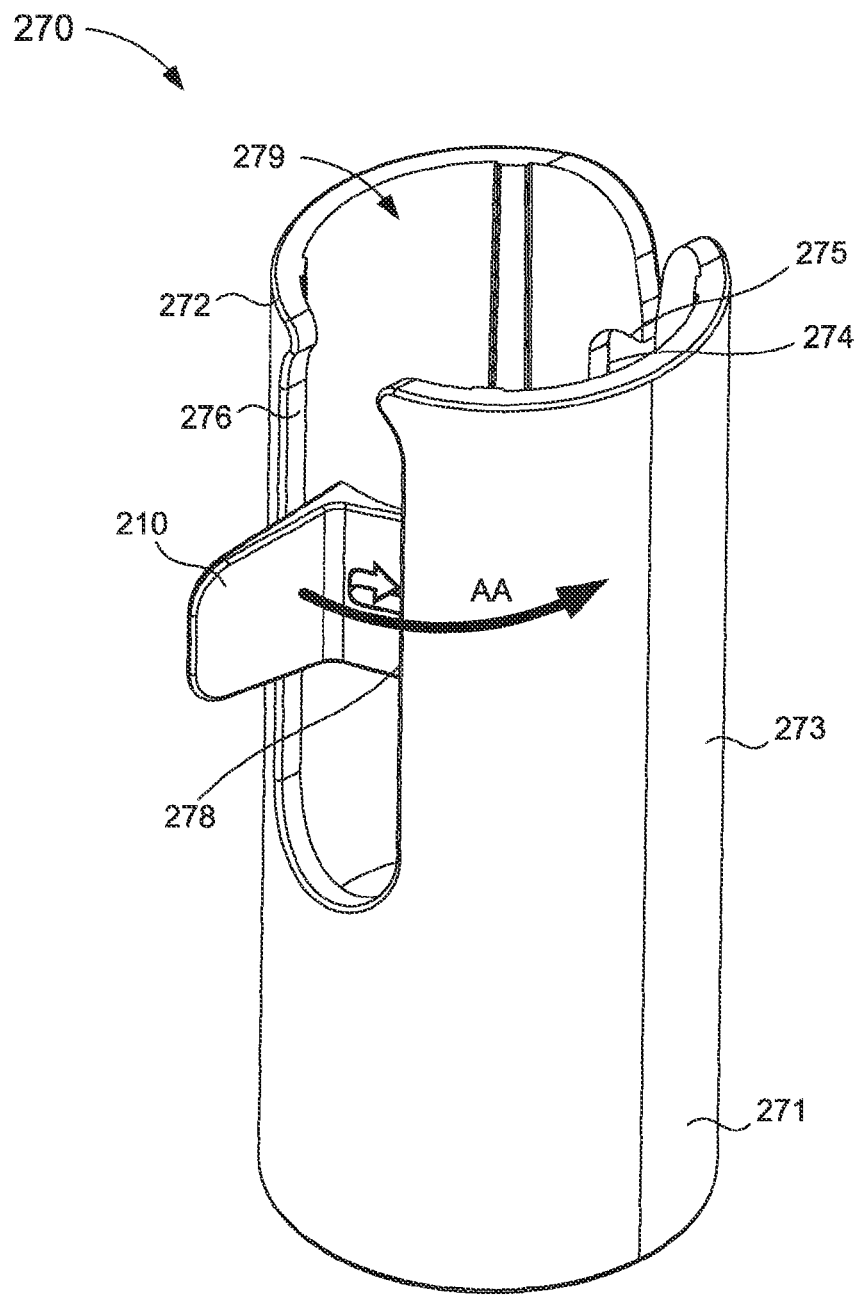
FIG. 6 is a perspective view of an actuator included in the bodily-fluid transfer device of FIG. 2.

As shown in FIG. 6, the actuator 270 includes a proximal end portion 271 and a distal end portion 272. The proximal end portion 271 is a substantially closed portion of the actuator 270 from which a set of annular walls 273 extend. The annular walls 273 define an inner volume 279 that can receive a portion of the housing 201 and a portion of the flow control mechanism 230. More specifically, the distal end portion 272 of the actuator 270 is substantially open such that the portion of the housing 201 and the portion of the flow control mechanism 230 can be disposed within the inner volume 279 of the actuator 270. In this manner, the actuator 270 can be moved between a first position (e.g., a proximal position) and a second position (e.g., a distal position), relative to the housing 201, to move the transfer device 200 between the first, second, and third configuration.

The walls 273 of the actuator 270 define a first channel 274 and a second channel 276. Expanding further, when the portion of the housing 201 is disposed within the inner volume 279 of the actuator 270, the outlet port 210 of the housing 201 extends through the first channel 274 and the inlet port 208 of the housing 201 extends through the second channel 276. In this manner, the outlet port 210 and the inlet port 208 of the housing 201 can move within the first channel 274 and the second channel 276, respectively, when the actuator 270 is moved between its first position and its second position, relative to the housing 201.

The actuator 270 further includes a tab 277 that can selectively engage the inlet port 208 when the inlet port 208 is disposed within the second channel 276. Expanding further, the tab 277 extends from a surface of the wall 273 of the actuator 270 and includes a deformable portion 278 that can be deformed to move the tab 277 from a first configuration to a second configuration, as indicated by the arrow AA in FIG. 6. In this manner, the tab 277 can selectively limit the movement of the actuator 270 from its first position to its second position, relative to the housing 201. Similarly, the wall 273 of the actuator 270 defining the first channel 274 is configured to form a shoulder 275 that can engage the retention tabs 213 (described above) of the housing 201. The arrangement of the shoulder 275 and the retention tabs 213 is such that the when in contact, the shoulder 275 and the retention tabs 213 collectively limit the movement of the actuator 270 from its second position to its first position, relative to the housing 201, as described in further detail herein.

Figure 7:
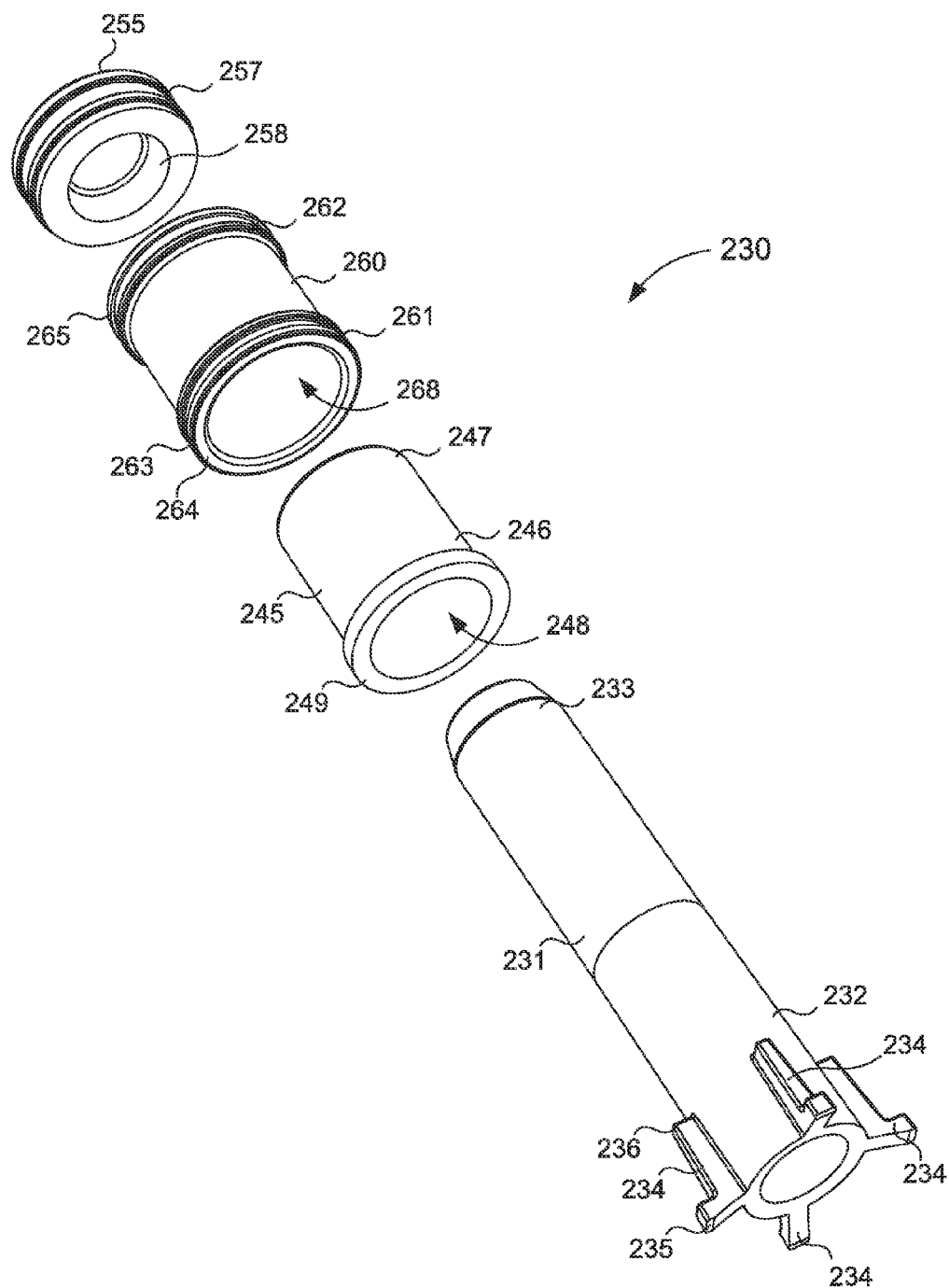
FIG. 7 is an exploded perspective view of a flow control mechanism included in the bodily-fluid transfer device of FIG. 2.
Figure 8:
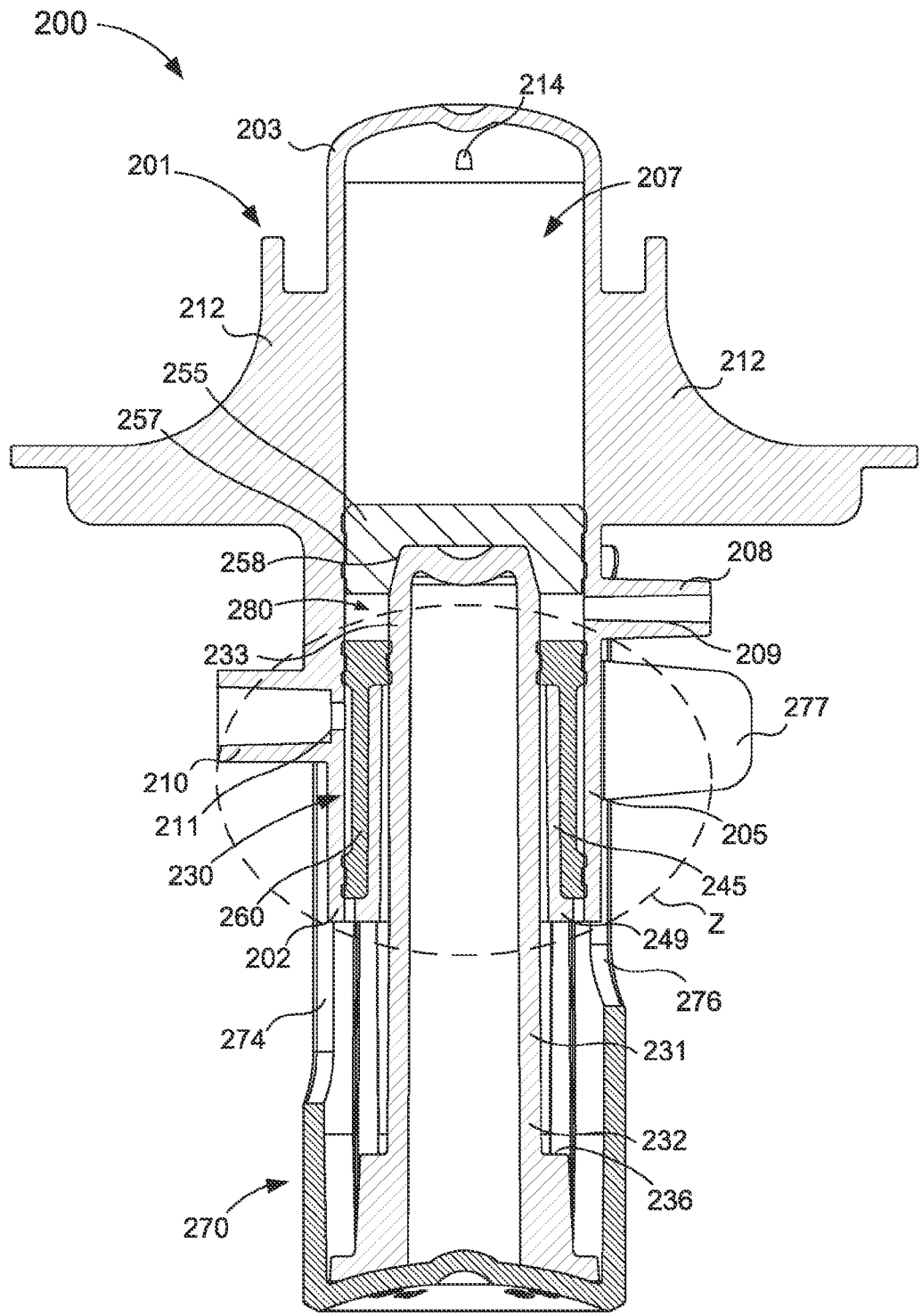
FIG. 8 is a cross-sectional view of the bodily-fluid transfer device of FIG. 2 taken along the line $X_1$-$X_1$, in a first configuration.
Figure 9:
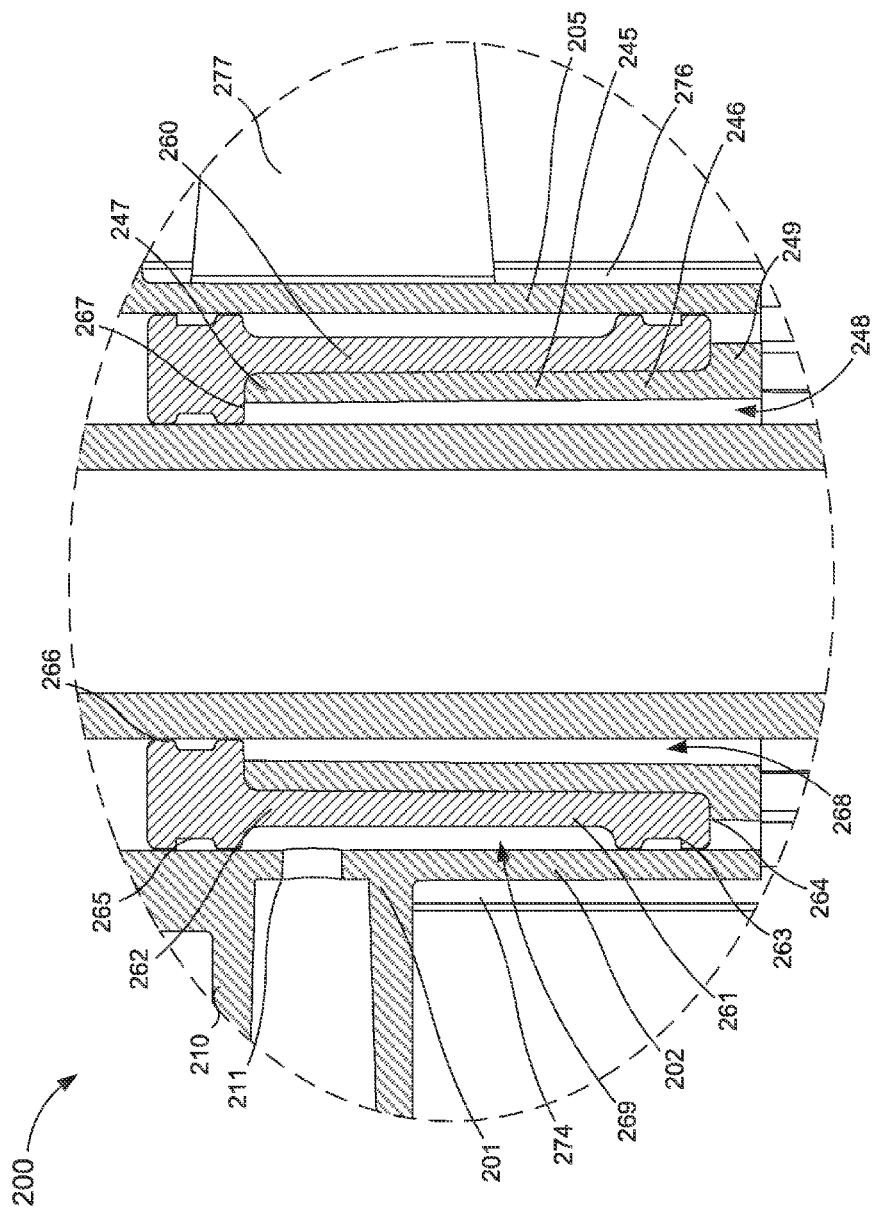
FIG. 9 is an enlarged view of the region labeled Z in FIG. 8.
Figure 10:
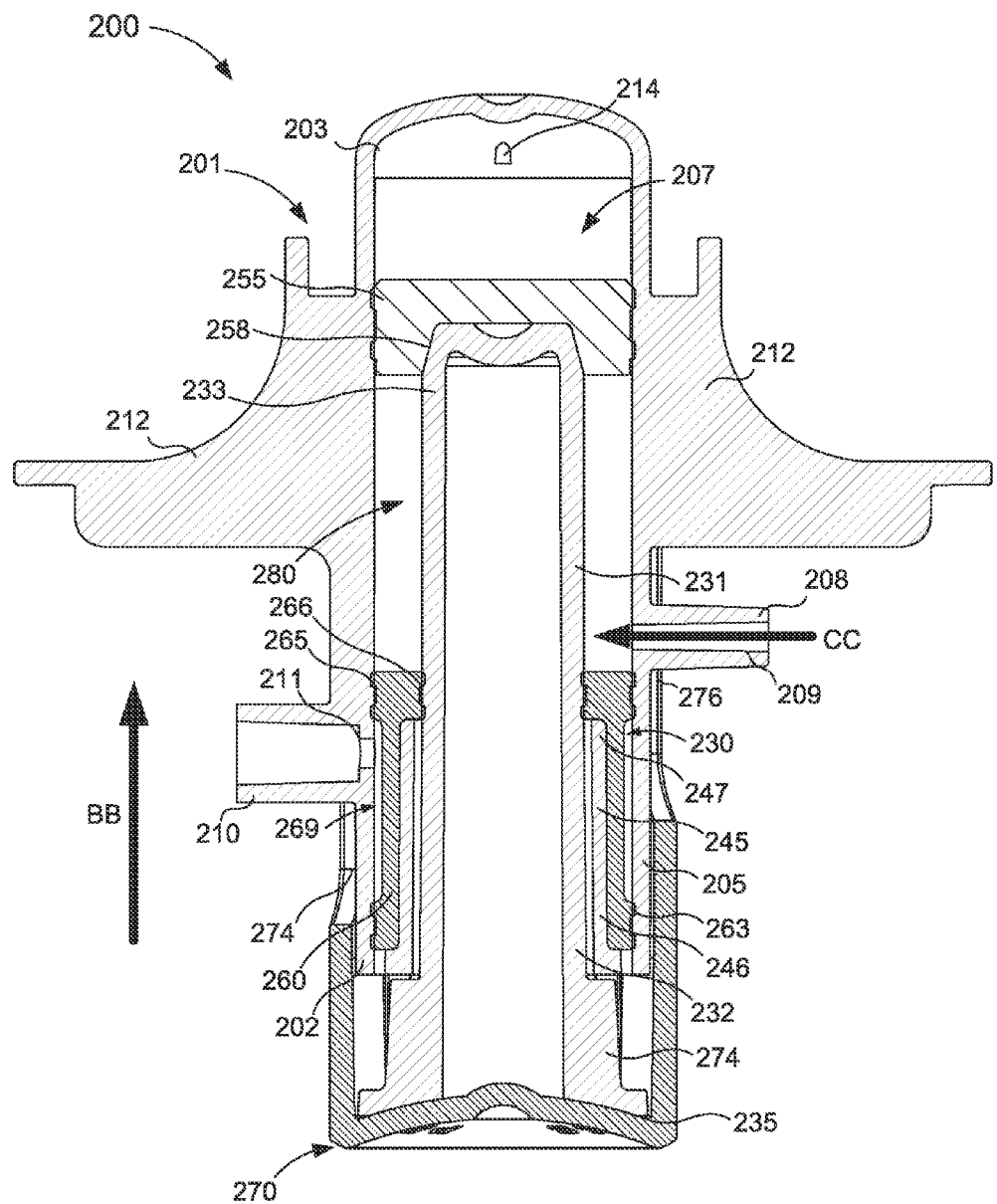
FIGS. 10 and 11 are cross-sectional views of the bodily-fluid transfer device of FIG. 2 taken along the line $X_1$-$X_1$, in a second and third configuration, respectively.

As shown in FIGS. 7-9, the flow control mechanism 230 includes a first control member 231, a second control member 245, a first plunger 255, and a second plunger 260. At least a portion of the flow control mechanism 230 is movably disposed within the inner volume 207 of the housing 201. More specifically, the flow control mechanism 230 can be disposed within the inner volume 207 of the housing 201 such that as the actuator 270 is moved from its first position to its second position, the flow control mechanism 230 is moved between a first, a second, and a third configuration, as further described herein.

As shown in FIG. 7, the first control member 231 is a substantially cylindrical elongate member and includes a proximal end portion 232 and a distal end portion 233. The distal end portion 233 is disposed within a portion of the first plunger 255. The proximal end portion 232 includes a set of protrusions 234 that extend outward from a surface of the proximal end portion 232. The protrusions 234 include a proximal surface 235, which can be placed in contact with a portion of the actuator 270, and a distal surface 236, which can be placed in contact with a portion of the second control member 245. Therefore, when the actuator 270 is moved from its first position to its second position relative to the housing 201, the actuator 270 can move the first control member 231 within the inner volume 207. Moreover, the movement of the first control member 231 within the inner volume 207 can be such that the flow control mechanism 230 is moved between its first, second, and third configurations, as further described herein. While shown in FIG. 7 as including four protrusions 234, in other embodiments, the first control member 232 can include any suitable number of protrusions 234. For example, in some embodiments, a first control member can include more than four protrusions. In other embodiments, a first control member can include fewer than four protrusions.

The second control member 245 includes a proximal end portion 246 and a distal end portion 247, and defines a void 248 therethrough. The proximal end portion 246 of the second control member 245 includes a collar 249 that is configured to circumscribe the proximal end portion 246. Similarly stated, the collar 249 has a diameter that is substantially larger than the diameter of the proximal end portion 246 of the second control member 245. The proximal end portion 246 and the distal end portion 247 are substantially open such that the second control member 245 is substantially annular. In this manner, the second control member 245 is configured to be movably disposed about a portion of the first control member 231 (see e.g., FIGS. 8 and 9).

As shown in FIG. 7, the first plunger 255 includes a seal element 257 and defines a recess 258. The recess 258 is configured to receive the distal end portion 233 of the first control member 231, as shown in FIG. 8. The first plunger 255 can be any suitable shape, size, or configuration. For example, in some embodiments, the first plunger 255 can have a diameter that substantially corresponds to an inner diameter of the walls 205 of the housing 201. More specifically, the diameter of the first plunger 255 can be substantially larger than the inner diameter of the walls 205 such that when the first plunger 255 is disposed within the inner volume 207 of the housing 201, the seal element 257 forms a substantially fluid tight seal with an inner surface of the walls 205. In this manner, the first plunger 255 can fluidically isolate a portion of the inner volume 207 that is distal to the first plunger 255 from a portion of the inner volume 207 that is proximal to the first plunger 255.

The second plunger 260 includes a proximal end portion 261 and a distal end portion 262, and defines an inner volume 268 therethrough. In this manner, the second plunger 260 can be disposed about the second control member 245. Similarly stated, the second plunger 260 can be substantially annular and can substantially circumscribe the second control member 245 such that the second control member 245 is disposed within the inner volume 268. The proximal end portion 261 includes a first seal element 263 that forms a shoulder 264 configured to be placed in contact with the collar 249 (described above) when the second plunger 260 is disposed about the second control member 245. Similarly, the distal end portion 262 includes a second seal element 265 and a third seal element 266 configured to form an inner shoulder 267. The inner shoulder 267 can be placed in contact with the distal end portion 247 of the second control member 245 when the second plunger 260 is disposed about the second control member 245.

As shown in FIG. 9, the first seal element 263 and the second seal element 265 are configured to extend beyond an outer surface of the second plunger 260. Similarly stated, the first seal element 263 and the second seal element 265 have a diameter that is at least slightly larger than a diameter of a portion of the second plunger 260 that is disposed between the first seal element 263 and the second seal element 265. Moreover, the diameter of the first seal element 263 and the second seal element 265 is configured to be at least slightly larger than the inner diameter of the walls 205 defining the inner volume 207. Thus, the first seal element 263 and the second seal element 265 form a substantially fluid tight seal with the inner surface of the walls 205. In addition, the diameter of the portion of the second plunger 260 that is disposed between the first seal element 263 and the second seal element 265 can be at least slightly smaller than the inner diameter of the walls 205. Therefore, the portion of the second plunger 260 (between the first and second seal elements 263 and 265) and the inner surface of the walls 205 define a void 269 that substantially circumscribes the portion of the second plunger 260. Furthermore, the first seal element 263 fluidically isolates the void 269 from a volume that is distal to the first seal element 263 and the second seal element 265 fluidically isolates the void 269 from a volume that is proximal to the second seal element 265.

The third seal element 266 is configured to extend beyond an inner surface of the second control member 245 such that when the first control member 231 is disposed within the void 248 of the second control member 245 (described above), the third seal element 266 forms a substantially fluid tight seal with an outer surface of the first control member 231. In this manner, the first control member 231 can be moved relative to the second control member 245 while fluidically isolating a volume that is proximal to the third seal element 266 from a volume that is distal to the third seal element 266, as further described herein.

The arrangement of the second plunger 260 and the second control member 245 can be such that the second control member 245 provides structural rigidity for the second plunger 260. In this manner, the flow control mechanism 230 can move within the inner volume 207 of the housing 201 without the first seal element 263, the second seal element 265, and/or the third seal element 266 deforming a sufficient amount to disrupt the substantially fluid tight seal or seals. While shown in FIGS. 2-12 as including a second control member 245 that is independent of the second plunger 260 (e.g., not monolithically formed), in other embodiments, the second plunger 260 and the second control member 245 can be monolithically formed while maintaining a desired structural rigidity.

Referring back to FIG. 8, the first reservoir 280 can be defined between a proximal surface of the first plunger 255 and the distal surface of the second plunger 260. More specifically, the first reservoir 280 is formed by a portion of the inner volume 207 of the housing 201 that is fluidically isolated between the first plunger 255 (e.g., the seal element 257) and the second plunger 260 (e.g., the second and third seal elements 265 and 266). In this manner, the first reservoir 280 can be an annular volume between the outer surface of the first control member 231 of the flow control mechanism 230 and the inner surface of the walls 205 defining the inner volume 207. Thus, the first reservoir 280 can be in fluid communication with the inlet port 208 of the housing 201 to receive an amount of a bodily-fluid and fluidically isolate the amount of the bodily-fluid from a volume substantially outside the first reservoir 280, as further described below.

As shown in FIG. 8, the transfer device 200 is in the first configuration when the actuator 270 is in its first position and the flow control mechanism 230 is in its first configuration. In this manner, a user can engage the transfer device 200 to couple the inlet port 208 to a proximal end portion of a lumen-defining device (not shown) such as, for example, a butterfly needle. With the inlet port 208 coupled to the lumen-defining device the inlet lumen 209 is placed in fluid communication with the lumen defined by the lumen-defining device. Furthermore, the distal end portion of the lumen-defining device can be disposed within a portion of the body of a patient (e.g., a vein), thus, the inlet lumen 209 is in fluid communication with the portion of the body of the patient. In a similar manner, the outlet port 210 can be coupled to an external fluid reservoir (not shown). The external fluid reservoir (i.e., the second reservoir) can be any suitable reservoir. For example, in some embodiments, the external fluid reservoir can be a BacT/ALERT® SN or a BacT/ALERT® FA, manufactured by BIOMERIEUX, INC. The outlet port 210 can be coupled to a needle and the transfer device 200 can include a container shroud (not shown) disposed about the needle and configured to receive a portion of the external fluid reservoir and protect the user from inadvertent needle sticks.

With the inlet port 208 coupled to the lumen-defining device and the outlet port 210 coupled to the external fluid reservoir, a user can place the transfer device 200 in the second configuration by moving the tab 277 of the actuator 270 to the second configuration. More specifically, the user can apply a force to bend the tab 277 about an axis defined by the deformable portion 278, thus, the tab 277 bends at the deformable portion 278, as indicated by the arrow AA in FIG. 6. In this manner, the tab 277 is moved relative to the inlet port 208 such that the tab 277 no longer limits the movement of the actuator 270 relative to the housing 201.

With the tab 277 no longer limiting the movement of the actuator 270, the user can engage the actuator and the engagement portion 212 of the housing 201 to apply an activation force on the actuator 270. In this manner, the actuator 270 and a portion of the flow control mechanism 230 are moved in the distal direction towards the second position, as shown by the arrow BB in FIG. 10, placing the transfer device in the second configuration. More specifically, in its first configuration, the first control mechanism 231 is arranged such that the proximal surfaces 235 of the protrusions 234 (described above) are in contact with the actuator 270 while the distal surfaces 236 of the protrusions 234 are spaced apart from the collar 249 of the second control member 245 (see FIG. 8). In this manner, a portion of the activation force is transferred to the first control member 231 to move the first control member 231 in the distal direction relative to the second control member 245 and the second plunger 260. Furthermore, with the distal end portion 233 of the first control member 231 disposed within the recess 258 of the first plunger 255, the first control member 231 moves the first plunger 255 in the direction of the arrow BB.

With the first plunger 255 forming a substantially fluid tight seal with the inner surface of the walls 205, the movement of the first plunger 255 relative to the housing 201 compresses air disposed within a portion of the inner volume 207 that is distal to the first plunger 255. In this manner, the vents 214 defined by the housing 201 (described above) can allow the air to exit the portion of the inner volume 207. Thus, the likelihood of the pressurized air within the portion of the inner volume 207 to disrupt the substantially fluid tight seal formed between the first plunger 255 and the inner surface of the walls 205 is reduced. Furthermore, the distal movement of the first control member 231 and the first plunger 255 relative to the second control member 245 and the second plunger 260 such that the height of the first reservoir 280 is increased (i.e., the volume of the first reservoir 280 is increased). With the first reservoir 280 fluidically isolated (as described above) the increase in the volume produces a negative pressure (i.e., vacuum) within the fluid reservoir 280.

As shown by the arrow CC, the inlet lumen 209 of the inlet port 208 defines a fluid flow path such that the fluid reservoir 280 is in fluid communication with the inlet port 208. Furthermore, with the inlet port 208 coupled to the lumen-defining device the fluid reservoir 280 is placed in fluid communication with the portion of the patient (e.g., the vein). The negative pressure within the fluid reservoir 280 is such that the negative pressure differential introduces a suction force within the portion of the patient. In this manner, a bodily-fluid is drawn into the fluid reservoir 280. In some embodiments, the bodily-fluid can contain undesirable microbes such as, for example, dermally-residing microbes. In some embodiments, the bodily-fluid can contain, for example, microbes dislodged from the keratin layer of the skin during the venipuncture. Moreover, the volume of the bodily-fluid drawn into the fluid reservoir 280 can be sufficiently large to collect at least a portion of the dermally-residing microbes while being sufficiently small such as to not compromise culture sensitively (e.g., blood culture sensitivity).

In some embodiments, the magnitude of the suction force can be modulated by increasing or decreasing the amount of activation force applied to the actuator 270. For example, in some embodiments, it can be desirable to limit the amount of suction force introduced to a vein. In such embodiments, the user can reduce the amount of force applied to the actuator 270 to reduce the rate at which the volume of the first reservoir 280 increases. In this manner, the suction force is reduced within the vein of the patient.

With the desired amount of bodily-fluid transferred to the fluid reservoir 280, a user can engage the transfer device 200 to move the transfer device 200 from the second configuration to the third configuration, wherein a flow of bodily-fluid is transferred to the external reservoir (e.g., such as those described above). In some embodiments, the desired amount of bodily-fluid transferred to the first reservoir 280 is a predetermined amount of fluid. For example, in some embodiments, the transfer device 200 can be configured to transfer bodily-fluid until the pressure within the first reservoir 280 is in equilibrium with the pressure of the portion of the body in which the lumen-defining device is disposed (e.g., the vein). In such embodiments, the equalizing of the pressure between the first reservoir 280 and the portion of the body stops the flow of the bodily-fluid into the first reservoir 280. In some embodiments, the predetermined amount of bodily-fluid (e.g., volume) is at least equal to the combined volume of the inlet lumen 209 and the lumen-defining device. In some embodiments, the predetermined amount of bodily-fluid can be, for example, approximately 2.25 mL. In other embodiments, the predetermined amount of bodily-fluid can be between approximately 0.5 mL and approximately 5 mL. Still in other embodiments, the predetermined amount of bodily-fluid can be as little as a single or few drops of fluid to between approximately 0.1 mL and 0.5 mL.

Figure 11:
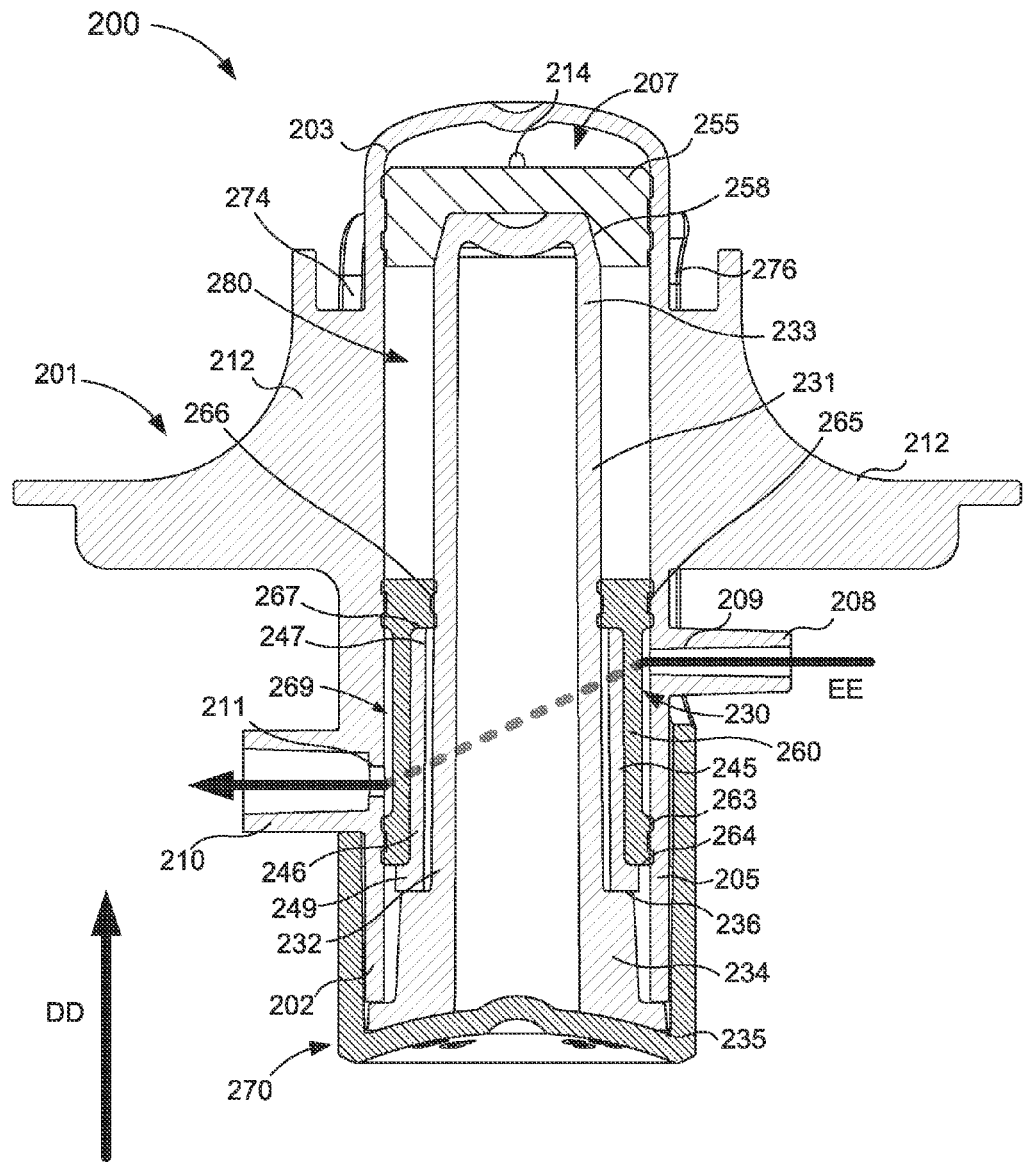

As shown in FIG. 11, the transfer device 200 can be moved from the second configuration to the third configuration by further moving the actuator 270 in the distal direction to a third position, as indicated by the arrow DD. Expanding further, the user can apply an activation force to the actuator 270 and the engagement portion 212 of the housing 201 such that the actuator 270 and the first control member 231 move in the distal direction. Moreover, as the actuator 270 is moved from the second configuration, the distal surfaces 236 of the protrusions 234 included in the first control mechanism 231 are brought into contact with the collar 249 of the second control member 245. Therefore, the first control member 231 transfers a portion of the activation force to the second control member 245 such that the second control member 245 and the second plunger 260 move concurrently with the first control member 231 and the first plunger 255 (i.e., the flow control mechanism 230 moves in the distal direction, relative to the housing 201). With the desired amount of the bodily-fluid disposed within the first reservoir 280 the volume of the first reservoir 280 is configured to remain constant as the flow control mechanism 230 moves relative to the housing 201. Similarly stated, the pressure within the fluid reservoir is configured to remain substantially unchanged as the transfer device 200 is moved from the second configuration to the third configuration.

The actuator 270 is configured to move the flow control mechanism 230 within the inner volume 207 of the housing 201 such that the first reservoir 280 is fluidically isolated from the inlet port 208. Moreover, the flow control mechanism 230 can be moved in the distal direction a sufficient amount such that the second seal element 265 of the second plunger 260 is moved to a distal position relative to the inlet lumen 209 defined by the inlet port 208. In addition, the distal movement of the flow control mechanism 230 is such that the first seal element 263 of the second plunger 260 is maintained in a proximal position relative to the outlet lumen 211 defined by the outlet port 210. In this manner, the void 269 (described above) is in fluid communication with the inlet lumen 209 and the outlet lumen 211.

As shown by the arrow EE, the inlet lumen 209 of the inlet port 208, the void 269, and the outlet lumen 211 of the outlet port 210 define a fluid flow path such that the external reservoir (not shown in FIG. 11) is in fluid communication with the inlet port 208 and, therefore, the portion of the patient (e.g., the vein). Furthermore, the external reservoir is configured to define a negative pressure (e.g., the known external reservoirs referred to herein are vessels defining a negative pressure). The negative pressure within the external reservoir is such that the negative pressure differential between the external reservoir and the portion of the body of the patient introduces a suction force within the portion of the patient. Therefore, a desired amount of bodily-fluid is drawn into the external reservoir and is fluidically isolated from the first, predetermined amount of bodily-fluid contained within the first reservoir 280. In this manner, the bodily-fluid contained in the external reservoir is substantially free from microbes generally found outside of the portion of the patient (e.g., dermally residing microbes, microbes within a lumen defined by the transfer device 200, microbes within the lumen defined by the lumen defining device, and/or any other undesirable microbe). With the desired amount of bodily-fluid contained in the external fluid reservoir, the external reservoir can be decoupled from the transfer device 200.

Figure 12:
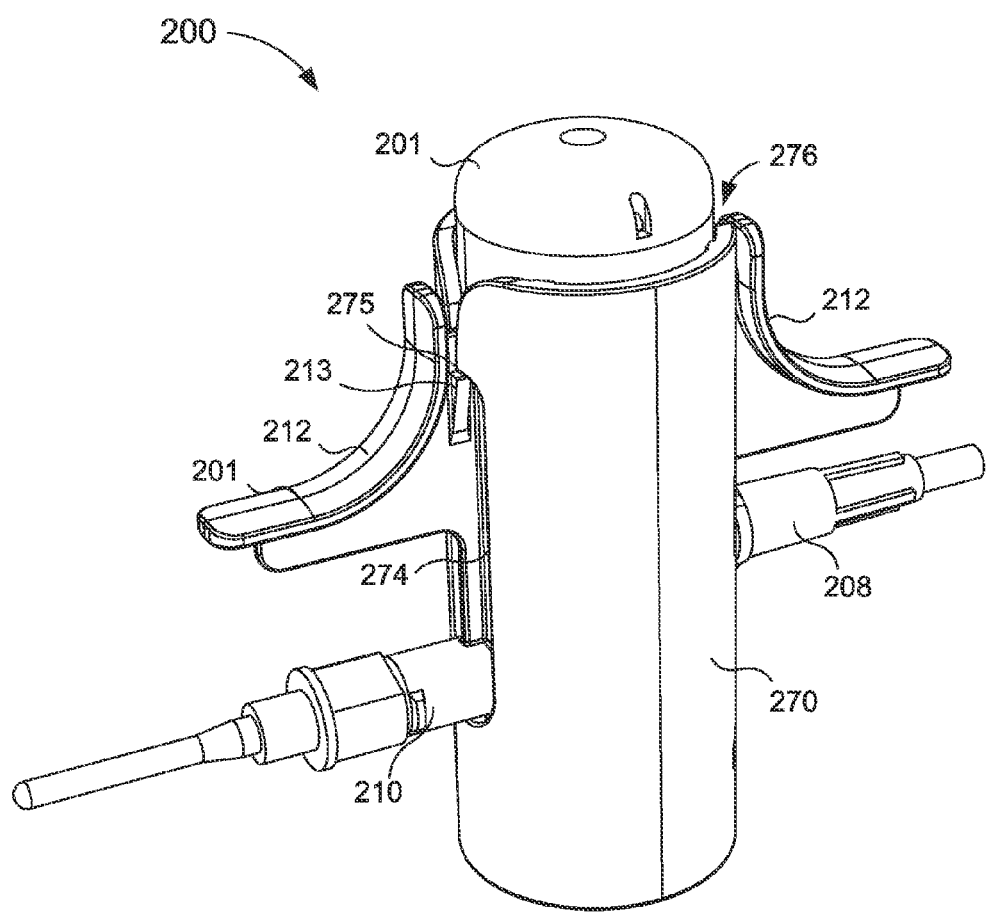
FIG. 12 is a perspective view of the bodily-fluid transfer device of FIG. 3, in the third configuration.

As shown in FIG. 12, the movement of the transfer device 200 to the third configuration is such that the retention tabs 213 (described above) are placed in contact with the shoulder 275 of the actuator 270 (described above). The retention tabs 213 and the shoulder 275 collectively maintain the transfer device 200 in the third configuration. Thus, the first amount of bodily-fluid contained within the first reservoir 280 is maintained in fluidic isolation from a volume outside of the fluid reservoir 280. In this manner, the transfer device 200 can be safely discarded or the volume of bodily fluid contained in the first reservoir 280 can be used for other testing such as, for example, testing where dermally residing microbes would not affect the test results.

While the transfer device 200 is shown and described in FIGS. 2-12 as including a discrete actuator 270, in some embodiments, a transfer device can include a fluid reservoir configured to actuate the transfer device. For example, FIGS. 13-19 illustrate a transfer device 300 according to an embodiment. The transfer device 300 includes a housing 301, a container shroud 320, a flow control mechanism 330 defining a first fluid reservoir 380, and a second fluid reservoir 390. The transfer device 300 can be any suitable shape, size, or configuration. For example, while shown in FIG. 13 as being substantially cylindrical, the transfer device 300 can be polygonal (rectangular, hexagonal, etc.), oval (elliptical, circular, etc.), and/or any other non-cylindrical shape. As further described below, the transfer device 300 can be moved between a first, a second, and a third configuration to deliver a flow of a bodily-fluid that is substantially free from microbes exterior the body, such as, for example, dermally residing microbes.

Figure 13:
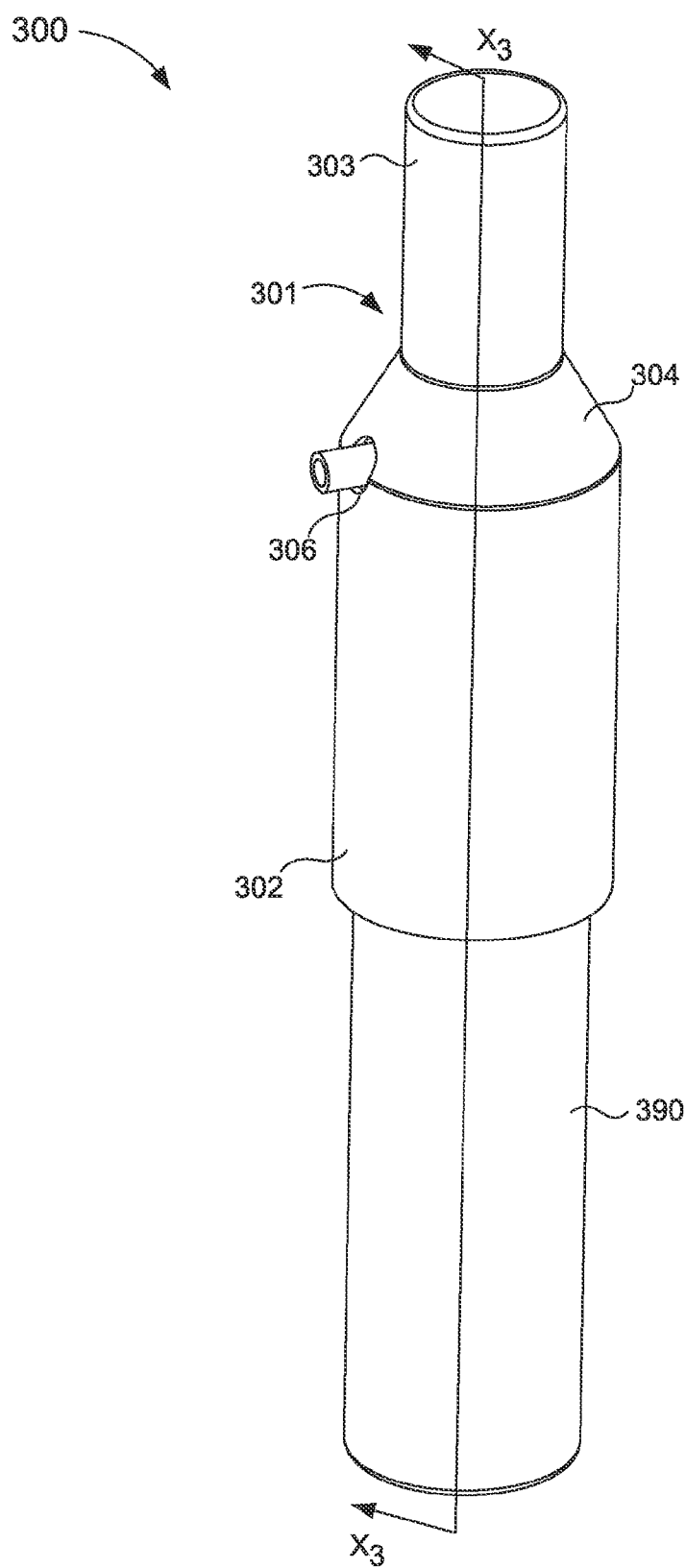
FIG. 13 is a perspective view of a bodily-fluid transfer device according to an embodiment.
Figure 14:
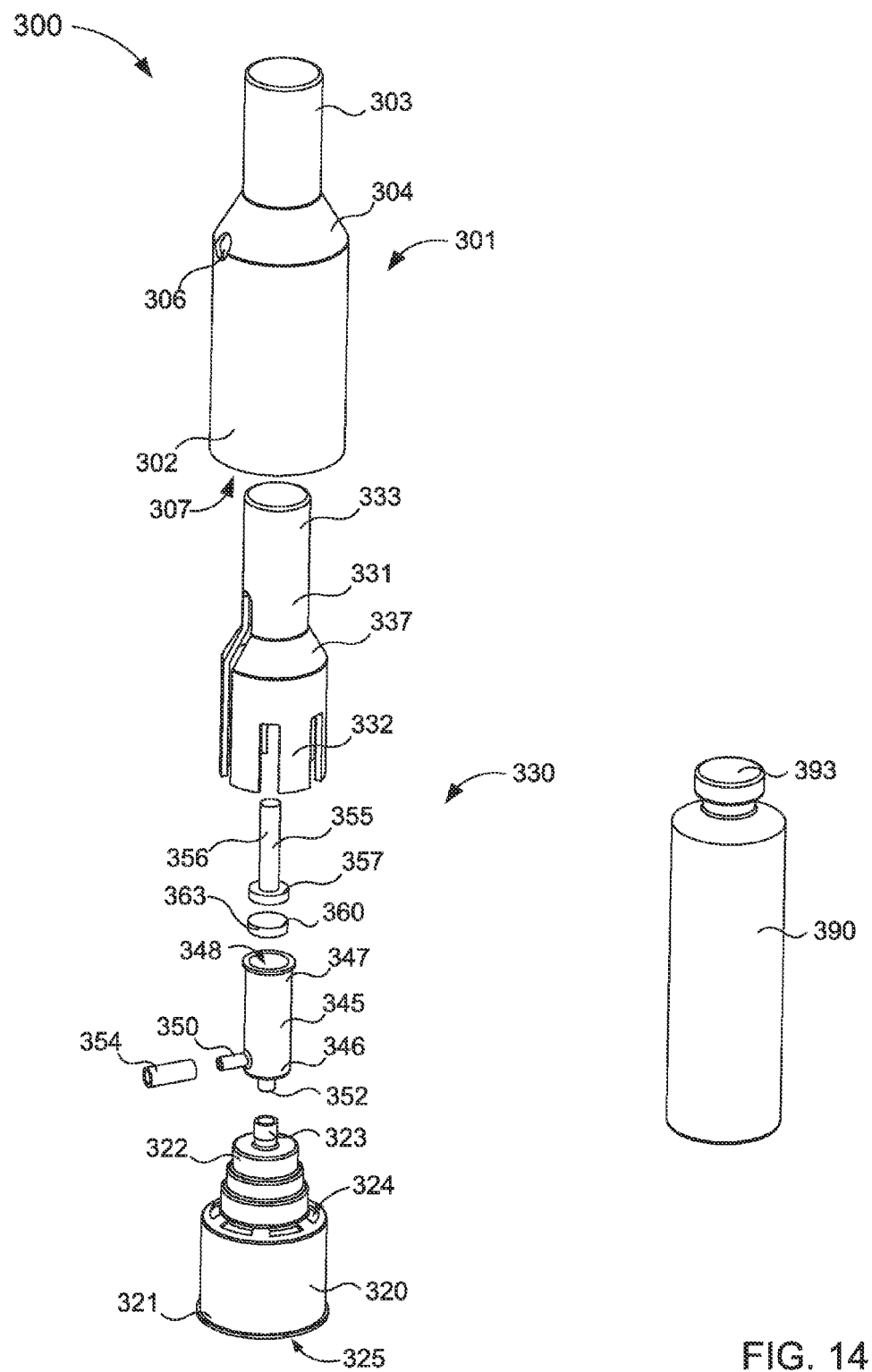
FIG. 14 is an exploded view of the bodily-fluid transfer device of FIG. 13.
Figure 15:
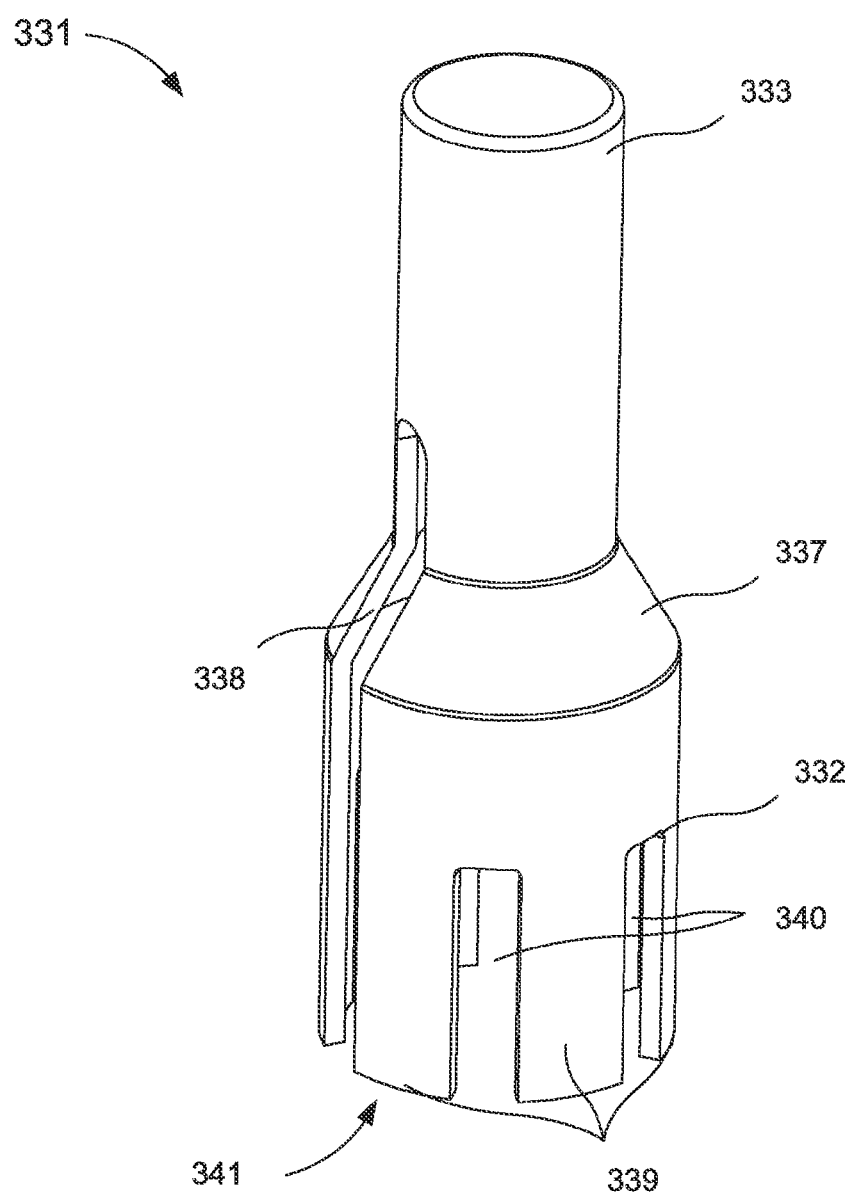
FIG. 15 is a perspective view of a first control member included in the bodily-fluid transfer device of FIG. 13.

As shown in FIGS. 13 and 14, the housing 301 includes a proximal end portion 302, a distal end portion 303, and a tapered portion 304, and defines an inner volume 307 and an aperture 306. The distal end portion 303 is a substantially closed portion of the housing 301 and extends in the proximal direction towards the tapered portion 304. The proximal end portion 302 of the housing 301 is substantially open such that the inner volume 307 can movably receive the flow control mechanism 330 and at least a portion of the second fluid reservoir 390. As shown, the proximal end portion 302 has a diameter that is substantially larger than a diameter of the distal end portion 303 of the housing 301. In this manner, the tapered portion 304 extends from the proximal end portion 302 towards the distal end portion 303 at a given angle such that the tapered portion 304 is a transitional portion between the larger diameter of the proximal end portion 302 and the smaller diameter of the distal end portion 303. The aperture 306 defined by the housing 301 receives a portion of the flow control mechanism 330, as further described herein.

As shown in FIG. 14, the flow control mechanism 330 includes a first control member 331, a second control member 345, a first plunger 355, and a second plunger 360. As described above, the flow control mechanism 330 is configured to be movably disposed within the inner volume 307 of the housing 301. More specifically, the flow control mechanism 330 can be moved within the housing 301 between a first, a second, and a third configuration.

The first control member 331 has a shape that substantially corresponds to the shape of the housing 301 and includes a proximal end portion 332, a distal end portion 333, and a tapered portion 337 disposed therebetween. The first control member 331 also defines an inner volume 341 (see e.g., FIG. 15) and a channel 338. The distal end portion 333 is a closed portion of the first control member 331 and is coupled to the first plunger 355, as further described herein. The proximal end portion 332 is substantially open such that the inner volume 341 can receive the second control member 345, the first plunger 355, and the second plunger 360. The proximal end portion 332 further includes a set of extensions 339 that define a set of slots 340. The extensions 339 can be movably disposed within a portion of the container shroud 320 and can be placed in contact with a portion of the second fluid reservoir 390, as further described herein. The channel 338 (FIG. 15) movably receives a portion of the second control member 345, as further described below.

The second control member 345 includes a proximal end portion 346, a distal end portion 347, and defines an inner volume 348. The distal end portion 347 is substantially open such that the inner volume 348 can receive at least a portion the first plunger 355 and the second plunger 360. The proximal end portion 346 includes an inlet port 350 and an outlet port 352. The inlet port 350 is in fluid communication with the inner volume 348 and extends from a portion of the wall of the second control member 345 defining the inner volume 348. Moreover, the inlet port 350 can be coupled to an adapter 354 (e.g., a Luer-Lok® or the like) such that when the flow control mechanism 330 is disposed within the housing 301, the adapter 354 extends through the channel 338 in the first control mechanism 331 and through the aperture 306 defined by the housing 301. The adapter 354 can further be fluidically coupled to a medical device (not shown) that defines a fluid flow pathway for withdrawing and/or conveying the bodily-fluid from a patient to the transfer device 300. For example, the adapter 354 can be fluidically coupled to a needle or other lumen-containing device (e.g., flexible sterile tubing) such that the inlet port 350 is in fluid communication with the lumen-containing device. Expanding further, when the lumen-containing device is disposed within a portion of a body of the patient (e.g., within a vein of the patient), the inner volume 348 of the second control member 345 is placed in fluid communication with the portion of the body of the patient. The outlet port 352 included in the second control member 345 is configured to be in fluid communication with the inner volume 348 and can be fluidically coupled to a portion of the container shroud 320, as further described herein.

As shown in FIG. 14, the first plunger 355 includes an elongate portion 356 and seal element 357. More specifically, the seal element 357 is disposed at a proximal end of the elongate portion 356. The seal element 357 can be substantially similar to the seal element 257 of the first plunger 255 described above with reference to FIGS. 7 and 8. Thus, the seal element 357 is configured to form a substantially fluid tight seal with an inner surface of the second control member 345. The seal element 357 can fluidically isolate a portion of the inner volume 348 that is distal to the first plunger 355 from a portion of the inner volume 348 that is proximal to the first plunger 355, as further described herein. The elongate portion 356 is configured to be coupled to the first control member 331 (e.g., via an adhesive, a mechanical fastener, or any other suitable coupling method). More specifically, the elongate portion 356 is configured to extend in the proximal direction from a surface of the first control member 331 (see e.g., FIG. 16).

The second plunger 360 includes a seal portion 363. The second plunger 360 is disposed within the inner volume 348 at a proximal position relative to the first plunger 355 (see e.g., FIG. 16). The seal member 363 is configured to form a substantially fluid tight seal with the inner surface of the second control member 345, as described above. While not shown in FIGS. 13-18, the second plunger 345 is configured to be coupled to the first plunger 355. For example, in some embodiments, the second plunger 345 can be coupled to the first plunger 355 via one or more tethers. In this manner, the first plunger 355 can be moved a first distance relative to the second plunger 360 to place the tethers in tension such that further movement of the first plunger 355 also moves the second plunger 360, as further described herein.

As shown in FIG. 14, the container shroud 320 includes a proximal end portion 321 and a distal end portion 322. The proximal end portion 321 is configured to receive a portion of the second fluid reservoir 390, as further described herein.

Figure 16:
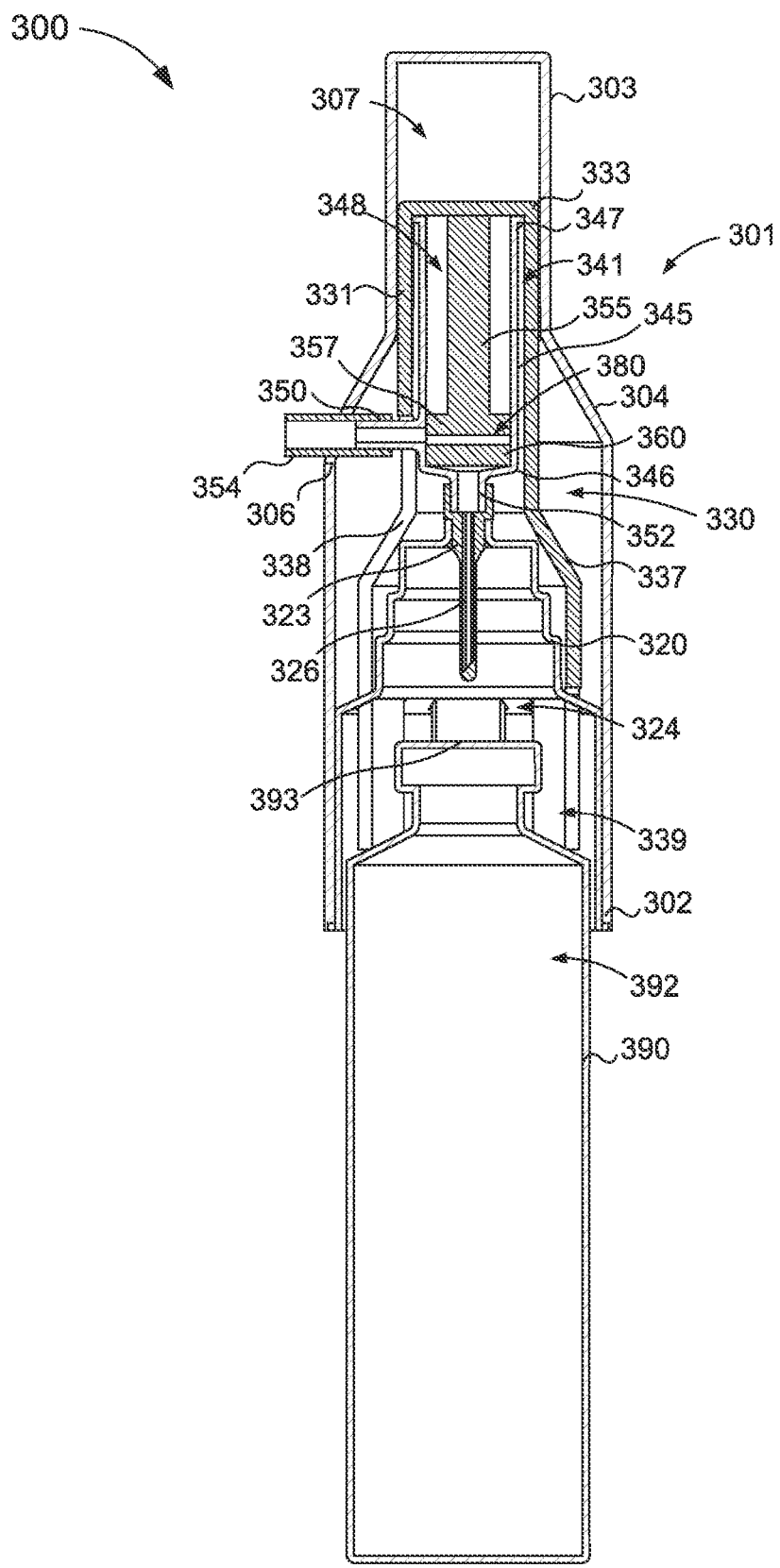
FIGS. 16-18 are cross-sectional views of the bodily-fluid transfer device taken along the line $X_3$-$X_3$ in FIG. 12, in a first, second, and third configuration, respectively.

The distal end portion 322 includes a port 323 that is coupled to the outlet port 352 of the second control member 345. In this manner, the port 323 included in the container shroud 320 can be placed in fluid communication with the inner volume 348 of the second control member 345. As shown in FIG. 16, the port 323 can be configured to include a needle 326 configured to pierce a portion of the second fluid reservoir 390, as described in further detail herein. The container shroud 320 is further configured to define a set of apertures 324 that movably receive the extensions 329 of the first control member 331. Similarly stated, at least a portion of the extensions 339 of the first control member 331 can be inserted into the apertures 324 defined by the container shroud 320.

Figure 17:
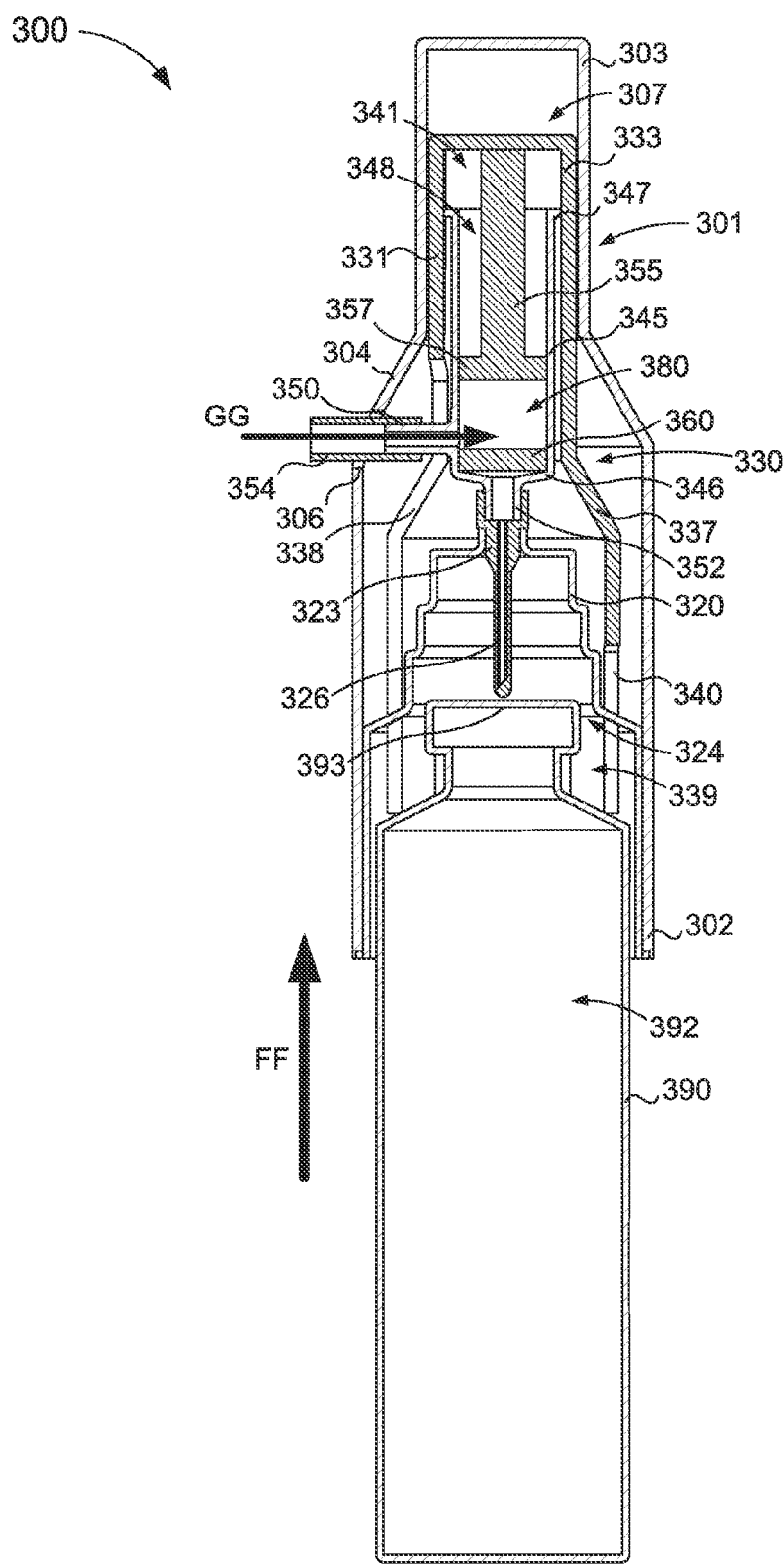
Figure 18:
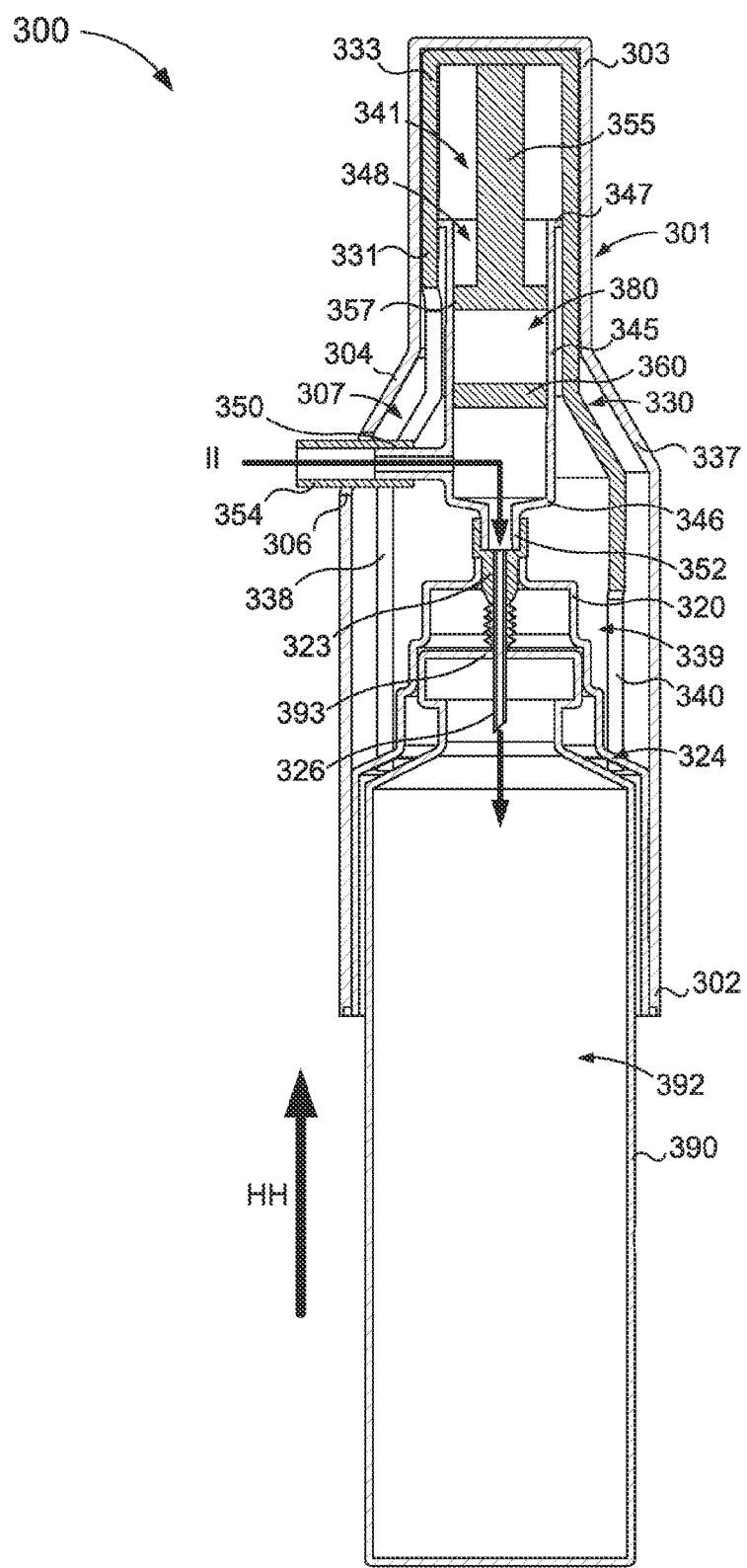

As shown in FIGS. 16-18, the first reservoir 380 can be defined between a proximal surface of the first plunger 355 and the distal surface of the second plunger 360. More specifically, the first reservoir 380 is formed by a portion of the inner volume 348 of the second control member 345 that is fluidically isolated between the first plunger 355 (e.g., the seal element 357) and the second plunger 360 (e.g., the seal elements 363). In this manner, the first reservoir 380 can be placed in fluid communication with the inlet port 350 of the second control member 345 to receive an amount of a bodily-fluid and can fluidically isolate the amount of the bodily-fluid from a volume substantially outside the first reservoir 380, as further described below.

At least a portion of the second reservoir 390 is disposed within the housing 301. More specifically, a portion of the second reservoir 390 is movably disposed within the container shroud 320 housed by the housing 301. The second reservoir 390 can be any suitable reservoir. For example, in some embodiments, the second fluid reservoir 390 can be a BacT/ALERT® SN or a BacT/ALERT® FA, manufactured by BIOMERIEUX, INC. The second reservoir 390 includes a piercable septum 393 that can be pierced by, for example, the needle 326 included in the port 323 of the container shroud 320 such that an inner volume 392 defined by the second reservoir 390 can receive a flow of the bodily-fluid. Moreover, the second reservoir 390 can be moved relative to the housing 301 to actuate the transfer device 300. Similarly stated, the second reservoir 390 can be moved relative to the housing 301 to move the transfer device 300 between the first, second, and third configurations, as described below.

As shown in FIG. 16, the transfer device 300 is in the first configuration when the second fluid reservoir 390 is in a first position (e.g., a proximal position) relative to the housing 301 and when the flow control mechanism 330 is in its first configuration. In this manner, a user can engage the transfer device 300 to couple the adapter 354 to a proximal end portion of a lumen-defining device (not shown) such as, for example, a butterfly needle. With the adapter 354 coupled to the lumen-defining device, the inlet port 350 is placed in fluid communication with the lumen defined by the lumen-defining device. Furthermore, the distal end portion of the lumen-defining device can be disposed within a portion of the body of a patient (e.g., a vein), thus, the inlet port 350 is in fluid communication with the portion of the body of the patient.

With the inlet port 350 coupled to the lumen-defining device, a user can place the transfer device 300 in the second configuration by moving the second reservoir 390 in the distal direction relative to the housing 301, as indicated by the arrow FF in FIG. 17. More specifically, the distal movement places a portion of the second reservoir 390 in contact with the extensions 339 of the first control member 331 such that the extensions 339 move within the apertures 324 defined by the container shroud 320. In this manner, the second reservoir 390 moves the first control member 331 within the inner volume 307 relative to the second control member 345.

With the first plunger 355 coupled to the first control member 331, the second reservoir 390 also urges the first plunger 355 to move within the inner volume 348 of the second control member 345 such that the flow control mechanism 330 is placed in its second configuration, as shown in FIG. 17. The distal movement of the first control member 331 and the first plunger 355 relative to the second control member 345 and the second plunger 360 is such that the height of the first reservoir 380 is increased (i.e., the volume of the first reservoir 380 is increased). With the first reservoir 380 fluidically isolated (as described above), the increase in the volume produces a negative pressure within the fluid reservoir 380.

As shown by the arrow GG, the inlet port 350 defines a fluid flow path such that the fluid reservoir 380 is in fluid communication with the inlet port 350. Furthermore, with the inlet port 350 coupled to the lumen-defining device (e.g., via the adapter 354) the fluid reservoir 380 is placed in fluid communication with the portion of the patient (e.g., the vein). The negative pressure within the fluid reservoir 380 is such that the negative pressure differential introduces a suction force within the portion of the patient. In this manner, a bodily-fluid is drawn into the fluid reservoir 380. In some embodiments, the bodily-fluid can contain undesirable microbes such as, for example, dermally-residing microbes.

With the desired amount of bodily-fluid transferred to the fluid reservoir 380, a user can move the transfer device 300 from the second configuration to the third configuration, wherein a flow of bodily-fluid is transferred to the second reservoir 390. In some embodiments, the desired amount of bodily-fluid transferred to the first reservoir 380 is a predetermined amount of fluid. For example, in some embodiments, the transfer device 300 can be configured to transfer bodily-fluid until the pressure within the first reservoir 380 is in equilibrium with the pressure of the portion of the body in which the lumen-defining device is disposed (e.g., the vein). In such embodiments, the equalizing of the pressure between the first reservoir 380 and the portion of the body stops the flow of the bodily-fluid into the first reservoir 380. In some embodiments, the predetermined amount of bodily-fluid (e.g., volume) is at least equal to the combined volume of the inlet port 350 and the lumen-defining device.

As shown in FIG. 18, the transfer device 300 can be moved from the second configuration to the third configuration by further moving the second reservoir 390 in the distal direction, as indicated by the arrow HH. The additional movement of the second reservoir 390 in the distal direction is such that the port 323 of the container shroud 320 is brought into contact with the second reservoir 390. More specifically, the needle 326 of the port 323 pierces the piercable septum 393 of the second reservoir 390 to place the port 323 in fluid communication with the inner volume 392 of the second reservoir 390.

In addition, as the second reservoir 390 is moved from the second configuration, the tethers (not shown) between the first plunger 355 and the second plunger 360 are placed in tension. Therefore, the first plunger 355 transfers a portion of the activation force (e.g., applied on the second reservoir 390 by the user) to the second plunger 360. In this manner, the second plunger 360 is moved concurrently with the first control member 331 and the first plunger 355 (e.g., the flow control mechanism 330 is moved to its third configuration). With the desired amount of the bodily-fluid disposed within the first reservoir 380 the volume of the first reservoir 380 is configured to remain constant as the flow control mechanism 330 moves relative to the housing 301. Similarly stated, the pressure within the fluid reservoir is configured to remain substantially unchanged as the transfer device 300 is moved from the second configuration to the third configuration.

When the flow control mechanism 330 is moved toward its third configuration, the first control member 331 is configured to move the first plunger 355, and the second plunger 360 within the inner volume 348 of the second control member 345 such that the first reservoir 380 is fluidically isolated from the inlet port 350. Moreover, the second plunger 360 can be moved in the distal direction a sufficient amount such that the second plunger 360 is moved to a distal position relative to the inlet port 350.

With the second plunger 360 in the distal position relative to the inlet port 350, the inlet port 350, a portion of the inner volume 348, the outlet port 350, and the port 323 define a fluid flow path, as indicated by the arrow II. In this manner, the inner volume 392 of the second reservoir is placed in fluid communication with the inlet port 350 and, therefore, the portion of the patient (e.g., the vein). Furthermore, the second reservoir 390 is configured to define a negative pressure (e.g., the known reservoirs referred to herein are vessels defining a negative pressure) such that the negative pressure differential between the second reservoir 390 and the portion of the body of the patient introduces a suction force within the portion of the patient. Therefore, a desired amount of bodily-fluid is drawn into the inner volume 392 of the second reservoir 390 and is fluidically isolated from the first, predetermined amount of bodily-fluid contained within the first reservoir 380. In this manner, the bodily-fluid contained in the second reservoir 390 is substantially free from microbes generally found outside of the portion of the patient (e.g., dermally residing microbes, microbes within a lumen defined by the transfer device 300, microbes within the lumen defined by the lumen defining device, and/or any other undesirable microbe). With the desired amount of bodily-fluid contained in the second reservoir 390, the second reservoir 390 can be decoupled from the transfer device 300. Furthermore, the first amount of bodily-fluid contained within the first reservoir 380 is maintained in fluidic isolation from a volume outside of the fluid reservoir 380. In this manner, the transfer device 300 can be safely discarded.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Additionally, certain steps may be partially completed and/or omitted before proceeding to subsequent steps.

While various embodiments have been particularly shown and described, various changes in form and details may be made. For example, although various embodiments have been described as having particular features and/or combinations of components, other embodiments are possible having any combination or sub-combination of any features and/or components from any of the embodiments described herein.

The specific configurations of the various components can also be varied. For example, the size and specific shape of the various components can be different than the embodiments shown, while still providing the functions as described herein. More specifically, the size and shape of the various components can be specifically selected for a desired rate of bodily-fluid flow into a fluid reservoir.

The invention claimed is:

1. A device for parenterally-procuring bodily-fluid samples from a patient, the device comprising:
    a housing including a proximal end portion and a distal end portion and defining an inner volume therebetween, the housing having an inlet port configured to be fluidically coupled to the patient and an outlet port configured to be fluidically coupled to a sample reservoir;
    a flow control mechanism including a first sealing member and a second sealing member disposed in the housing and defining a first fluid flow path and a second fluid flow path;
    a fluid reservoir disposed in the inner volume and at least partially defined by the flow control mechanism, the fluid reservoir configured to receive and isolate a first volume of bodily-fluid withdrawn from the patient; and
    an actuator operably coupled to the flow control mechanism and configured to move the first sealing member a first distance to form a negative pressure in the fluid reservoir when actuated by a user, the actuator further configured to move the first sealing member and the second sealing member a second distance to move the flow control mechanism from a first configuration, in which the inlet port is placed in fluid communication with the fluid reservoir such that bodily fluid can flow from the inlet port, through the first fluid flow path and to the fluid reservoir, to a second configuration, in which the inlet port is placed in fluid communication with the outlet port such that the bodily fluid can flow from the inlet, through the second fluid flow path and to the outlet.

2. The device of claim 1, wherein the outlet port is fluidically isolated from the fluid reservoir.

3. The device of claim 1, wherein the proximal end portion is substantially open.

4. The device of claim 1, wherein the distal end portion includes a vent.

5. The device of claim 1, wherein the fluid reservoir is defined at least in part by the first sealing member and the second sealing.

6. The device of claim 1, wherein the flow control mechanism includes a first control member coupled to a first sealing member and a second control member coupled to a second sealing member,
    the first control member configured to move the first sealing member a first distance when the actuator is actuated by the user, and
    the second control member configured to move the second sealing member a second distance after the first control member has moved the first sealing member the first distance.

7. A device for parenterally-procuring bodily-fluid samples from a patient, the device comprising:
    a housing including a proximal end portion and a distal end portion and defining an inner volume therebetween, the housing having an inlet port and an outlet port;
    a flow control mechanism movably disposed in the housing, the flow control mechanism including a first control member operably coupled to a first sealing member and a second control member operably coupled to a second sealing member, the flow control mechanism operable to selectively control fluid flow between the inlet port and at least one of the outlet and a fluid reservoir defined at least in part by the first sealing member and the second sealing member, the flow control mechanism having a first configuration such that fluid communication is established between the inlet port and the fluid reservoir, and a second configuration such that fluid communication is established between the inlet port and the outlet port; and an actuator operably coupled to the flow control mechanism and configured to move the first control member and the first sealing member a first distance to form a negative pressure in the fluid reservoir when actuated by a user, the actuator further configured to move the second control member and the second sealing member a second distance to place the flow control mechanism in the second configuration.

8. The device of claim 7, wherein the actuator is further configured to move the first sealing member and the second sealing member a second distance to place the flow control mechanism in the second configuration.

9. The device of claim 7, wherein the inlet port is axially offset from the outlet port such that the second sealing member fluidically isolates the inlet port from the outlet port in a first position and fluidically couples the inlet port and the outlet port in second position.

10. The device of claim 7, wherein the inlet port is radially offset from the outlet port.

11. The device of claim 7, wherein the second sealing member includes a first seal element in contact with the housing and a second seal element spaced apart from the first seal element and in contact with the housing, the first seal element and the second seal element defining an annular void therebetween such that the bodily fluid can flow from the inlet, through the annular void and to the outlet when the flow control mechanism is in the second configuration.

12. The device of claim 11, wherein the second sealing member is slidably disposed on a control member, the control member configured to move the first sealing member when the actuator is actuated by the user.

13. The device of claim 12, wherein the second sealing member includes a third seal element in contact with the control member.

* * * * *